(12) United States Patent
Parlato et al.

(10) Patent No.: US 12,029,437 B1
(45) Date of Patent: Jul. 9, 2024

(54) HAND PIECE FOR POWERED OSTEOTOME

(71) Applicant: HENRY SCHEIN, INC., Melville, NY (US)

(72) Inventors: Brian David Parlato, Hillsborough, NJ (US); Alfred Anthony Litwak, Keyport, NJ (US)

(73) Assignee: Henry Schein, Inc., Melville, NY (US)

( * ) Notice: Subject to any disclaimer, the term of this patent is extended or adjusted under 35 U.S.C. 154(b) by 370 days.

(21) Appl. No.: 17/402,511

(22) Filed: Aug. 14, 2021

Related U.S. Application Data

(60) Provisional application No. 63/066,089, filed on Aug. 14, 2020.

(51) Int. Cl.
| | |
|---|---|
| *A61B 17/16* | (2006.01) |
| *A61B 17/00* | (2006.01) |
| *F16J 1/02* | (2006.01) |
| *F16J 10/04* | (2006.01) |

(52) U.S. Cl.
CPC ............ *A61B 17/1613* (2013.01); *F16J 1/02* (2013.01); *F16J 10/04* (2013.01); *A61B 2017/00367* (2013.01); *A61B 2017/00477* (2013.01)

(58) Field of Classification Search
CPC ............... A61B 17/142; A61B 17/144; A61B 17/32002; A61B 17/32008; A61B 17/16–1697

See application file for complete search history.

(56) References Cited

U.S. PATENT DOCUMENTS

| | | | |
|---|---|---|---|
| 2,547,224 | A | 4/1951 | MacGuire |
| 2,716,971 | A | 9/1955 | Sykes |
| 2,995,113 | A | 8/1961 | Alois |
| 3,071,114 | A | 1/1963 | Hardy, Sr. |
| 3,127,197 | A | 3/1964 | Kretzschmar |
| 4,363,365 | A | 12/1982 | Nikolaev et al. |
| 4,594,939 | A | 6/1986 | van Os |
| 4,862,972 | A * | 9/1989 | Sudinshnikov .......... B25D 9/20 91/47 |

(Continued)

FOREIGN PATENT DOCUMENTS

| | | |
|---|---|---|
| CN | 203594594 U | 5/2014 |
| DE | 102008043098 B4 | 6/2013 |

(Continued)

OTHER PUBLICATIONS

High Performance Fluoropolymer Bearings Rulon, brochure from Tristar Saint-Gobain Performance Plastics Corporation, 2019.

*Primary Examiner* — Matthew J Lawson
(74) *Attorney, Agent, or Firm* — Perilla Knox & Hildebrandt LLP

(57) ABSTRACT

Provided is an osteotome handpiece that may be driven by compressed gas. In an embodiment, a spherical piston may be movable inside a cylinder having a liner, which may be made of a low-friction material such as a fluoropolymer. The spherical piston may impact a blade holder that transmits force to a blade. A piston return spring may be provided, along with a piston washer to avoid any possible outward deformation of the spring. The blade holder may be retained by a split and threaded retaining collar. Single-stroke or multi-stroke operation may be chosen by the user. The device has long-operating low-maintenance advantages.

18 Claims, 24 Drawing Sheets

(56) References Cited

U.S. PATENT DOCUMENTS

| | | | |
|---|---|---|---|
| 4,938,297 A * | 7/1990 | Schmidt | E21B 7/068 |
| | | | 173/133 |
| 5,178,410 A | 1/1993 | Thuen et al. | |
| 5,237,134 A | 8/1993 | Thuen et al. | |
| 5,352,230 A * | 10/1994 | Hood | B25D 9/08 |
| | | | 606/86 R |
| 6,832,605 B2 | 12/2004 | Farrell | |
| 6,889,682 B2 | 5/2005 | Styles et al. | |
| 6,908,271 B2 | 6/2005 | Breslin et al. | |
| 7,493,882 B2 | 2/2009 | Hiraishi et al. | |
| 7,735,811 B2 | 6/2010 | Pare et al. | |
| 7,779,930 B2 | 8/2010 | Lohmann et al. | |
| 7,934,896 B2 | 5/2011 | Schnier | |
| 8,011,443 B2 * | 9/2011 | Meixner | B25D 11/125 |
| | | | 173/202 |
| 8,015,907 B2 | 9/2011 | Tippmann, Sr. | |
| 8,181,460 B2 | 5/2012 | McQuary et al. | |
| 8,413,742 B2 | 4/2013 | Ikuta et al. | |
| 8,505,798 B2 | 8/2013 | Simonelli et al. | |
| 8,534,184 B2 | 9/2013 | Riley et al. | |
| 8,668,972 B2 | 3/2014 | Lewis et al. | |
| 8,720,599 B2 | 5/2014 | Ikuta | |
| 8,722,178 B2 | 5/2014 | Ashmead et al. | |
| 9,038,525 B2 | 5/2015 | Sullivan | |
| 9,080,605 B2 | 7/2015 | Karaki et al. | |
| 9,434,062 B2 | 9/2016 | Kamegai | |
| 9,695,861 B2 | 7/2017 | Steffl | |
| 9,957,785 B2 | 5/2018 | Boyd et al. | |
| 10,414,034 B2 | 9/2019 | Lilja et al. | |
| 10,495,352 B2 | 12/2019 | Barclay et al. | |
| 10,541,573 B2 | 1/2020 | Semken et al. | |
| 10,830,228 B2 | 11/2020 | Zimmerman, Jr. | |
| 10,835,680 B2 | 11/2020 | Cowan et al. | |
| 10,871,246 B2 | 11/2020 | Marici et al. | |
| 2004/0177989 A1 | 9/2004 | Nass et al. | |
| 2010/0313742 A1 | 12/2010 | Silva | |
| 2016/0121472 A1 | 5/2016 | Comarmond | |
| 2019/0365967 A1 * | 12/2019 | Vogt | A61B 17/142 |
| 2022/0025829 A1 | 1/2022 | Kuromasa et al. | |

FOREIGN PATENT DOCUMENTS

| | | |
|---|---|---|
| JP | 5100272 B2 | 12/2012 |
| RU | 2169328 C1 | 6/2001 |
| RU | 2479672 C1 | 4/2013 |
| WO | 2007112771 A1 | 10/2007 |
| WO | 2017213503 A1 | 12/2017 |

* cited by examiner

Fig. 1E    600

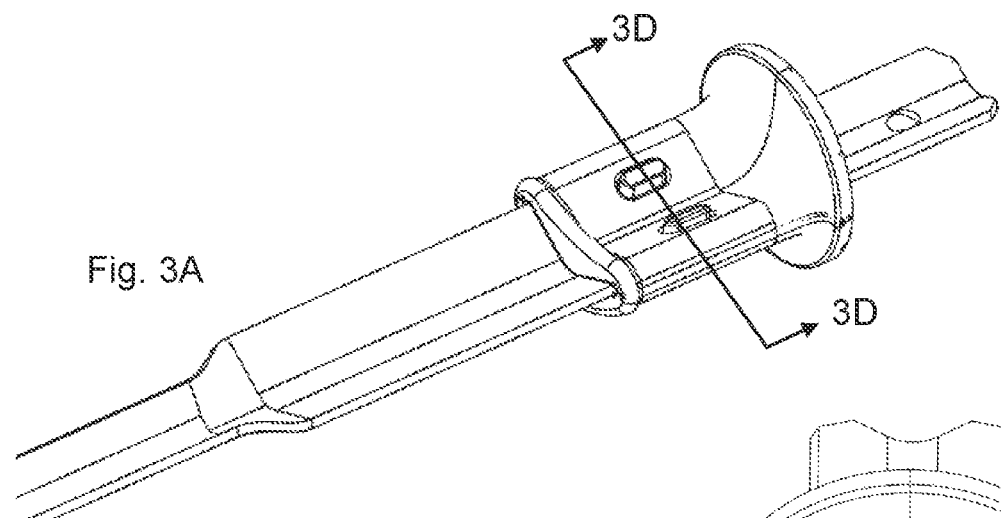
Fig. 3A
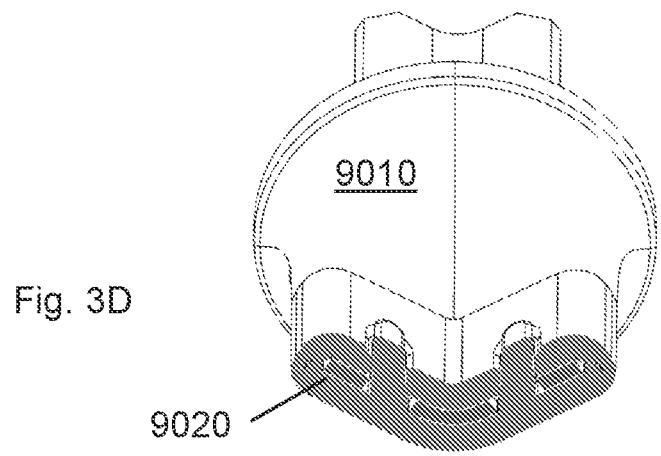
Fig. 3D
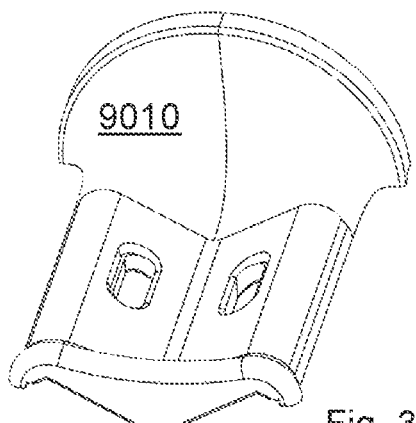
Fig. 3B
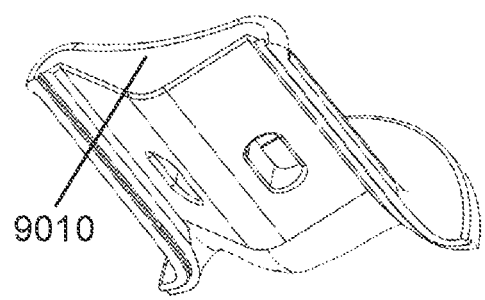
Fig. 3C
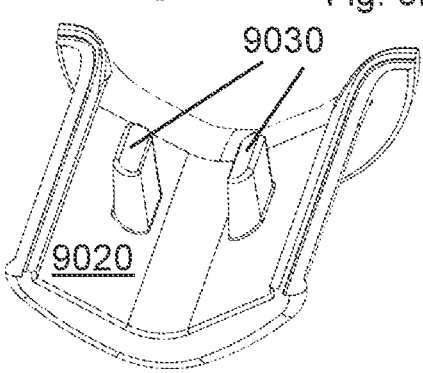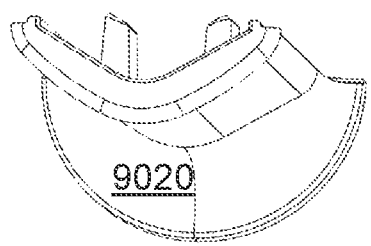

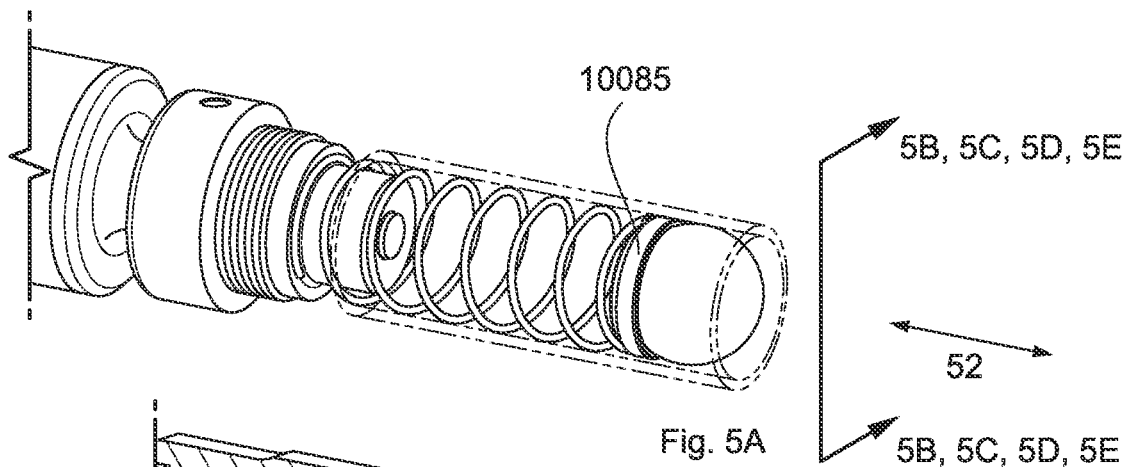
Fig. 5A
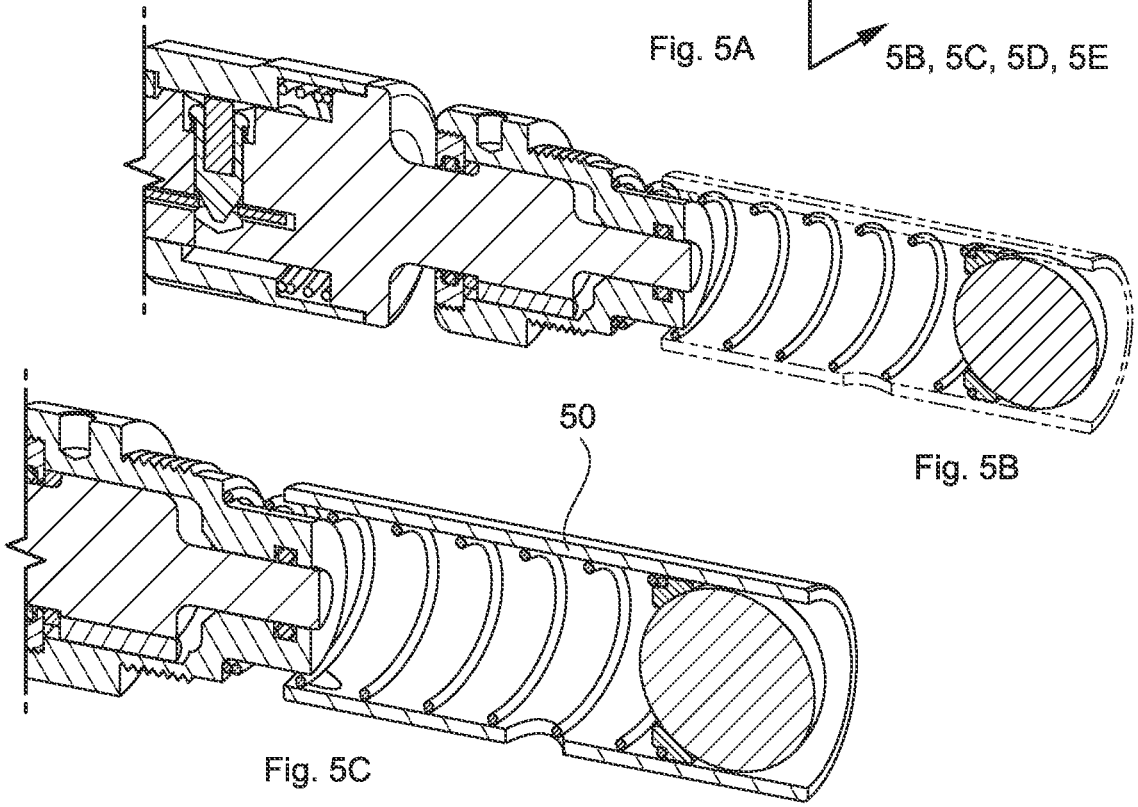
Fig. 5B
Fig. 5C
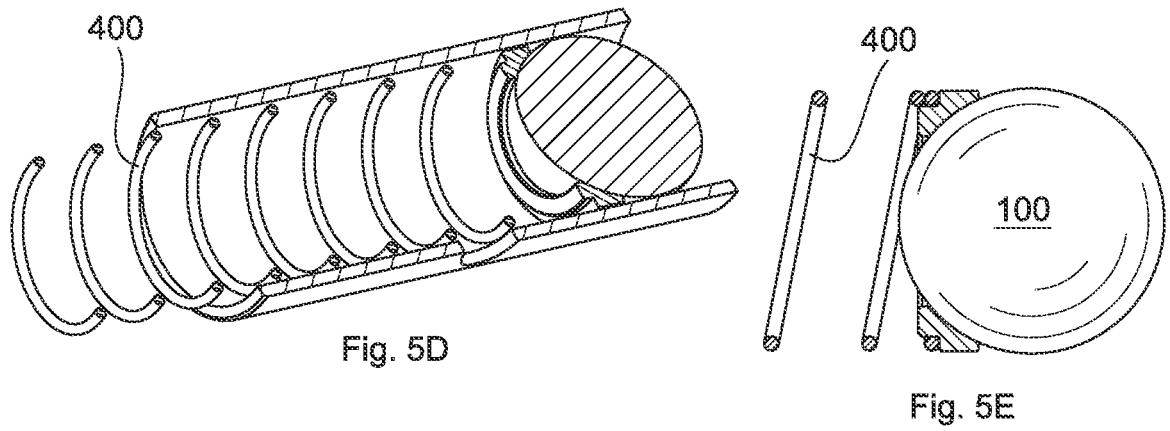
Fig. 5D
Fig. 5E

10037

10037

375

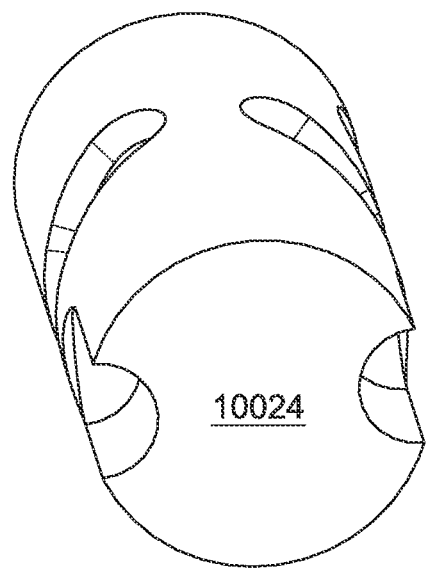
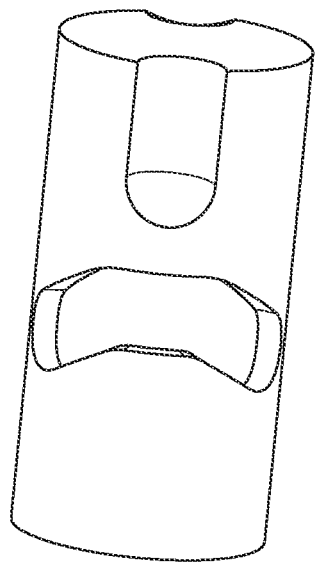
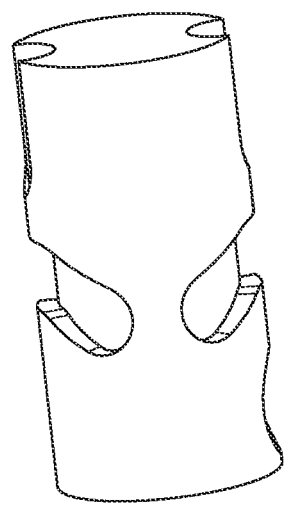
Fig. 10A  Fig. 10B  Fig. 10C
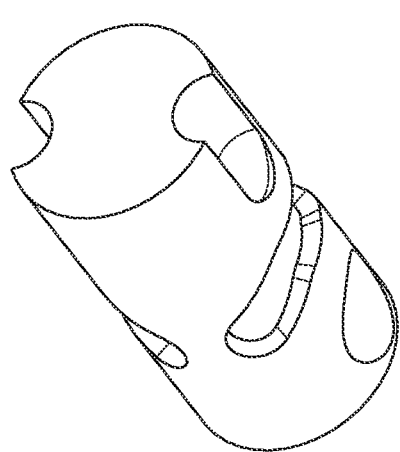
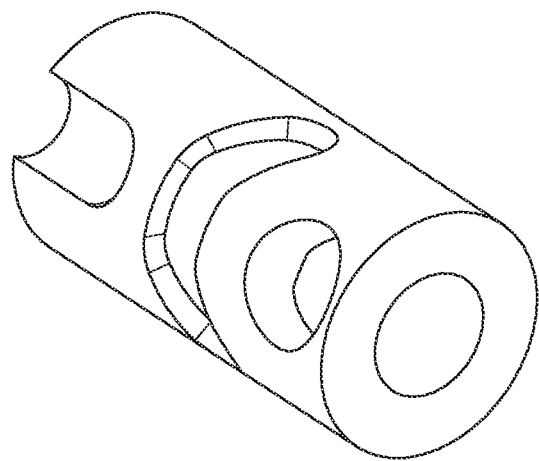
Fig. 10D  Fig. 10E Auto mode Safe mode Single mode

1212

Exhaust flowpath

External connector

Exhaust flowpath splitting into two halves and passing round the exterior of the trigger Exhaust flowpath

100

HAND PIECE FOR POWERED OSTEOTOME

CROSS-REFERENCE TO RELATED APPLICATION

This patent application claims the benefit of U.S. Provisional patent application Ser. No. 63/066,089 filed Aug. 14, 2020, which is hereby incorporated by reference in its entirety.

FIELD OF THE INVENTION

Embodiments of the invention pertain to cutting tools and orthopedic surgery.

BACKGROUND OF THE INVENTION

Various forms of powered osteotomes exist. In orthopedic surgery, it has historically been a difficult task to cut through bone cement that already exists in the body of the patient such as from a previous surgery at the same site. Accordingly, improvements in reliability and ease of use of osteotomes are still needed.

BRIEF SUMMARY OF THE INVENTION

In an embodiment of the invention, there may be provided an osteotome, comprising: a blade suitable to cut materials during surgery; and a drive mechanism that either is configured to transmit a force to a force-transmitting component that transmits force to the blade, or is configured to transmit force directly to the blade, wherein the drive mechanism comprises a cylinder having a cylinder liner, made of or comprising a cylinder liner material, and comprises a piston, made of or comprising a piston material, the piston being movable within the cylinder liner, wherein a coefficient of sliding friction of the cylinder liner material with the piston material is less than 0.20, or a coefficient of sliding friction of the cylinder liner material with itself is less than 0.20.

In an embodiment of the invention, there may be provided an osteotome, comprising: a blade suitable to cut materials during surgery; a drive mechanism that either is configured to transmit a force to a force-transmitting component that transmits force to the blade, or is configured to transmit force directly to the blade, wherein the drive mechanism comprises a cylinder, wherein the drive mechanism further comprises a piston, the piston being movable within the cylinder, wherein the drive mechanism further comprises a piston return spring located within the cylinder, wherein the drive mechanism further comprises a piston washer, the piston washer being located within the cylinder between the piston and the piston return spring, wherein the piston washer has a central opening therethrough, wherein when the piston is in contact with the piston washer, the piston is able to transmit force to either the force-transmitting component or the blade.

In an embodiment of the invention, there may be provided an osteotome, comprising: a blade suitable to cut materials during surgery; and a drive mechanism that is configured to transmit a force to a force-transmitting component that transmits force to a blade, wherein the drive mechanism comprises a cylinder and a piston movable within the cylinder, wherein the force-transmitting component is retained within the osteotome by a retaining collar that is externally threaded with a helical thread, and wherein the retaining collar comprises two parts each of which makes up approximately half of a circumference of the retaining collar and contains a portion of the thread.

BRIEF DESCRIPTION OF THE SEVERAL VIEWS OF THE ILLUSTRATIONS

Embodiments of the invention are further described but are in no way limited by the following illustrations.

FIG. 1A is a three-dimensional external view of an osteotome of an embodiment of the invention, also showing the midplane. FIG. 1B is a cross-sectional view of the same. FIG. 1C is a side section similar to FIG. 1B. FIG. 1D is a close-up of the piston (rearward) region. FIG. 1E is a close-up showing the blade holder. FIG. 1F is an alternate piston geometry that is cylindrical. FIG. 1G is an alternate piston geometry that is cylindrical with recesses. FIG. 1H is an alternate piston geometry that is a truncated ellipsoid. FIG. 1I is an alternate piston geometry that is spheres joined to each other.

FIG. 2A is a three-dimensional view of a blade of an embodiment of the invention, also showing the midplane and designation of directions. FIG. 2B is a close-up of the gripping region of the blade of FIG. 2A.

FIG. 3A is a three-dimensional view of the blade together with a two-piece splash guard. FIG. 3B shows the two pieces of the splash guard exploded away from each other, viewed somewhat from above. FIG. 3C shows the two pieces of the splash guard exploded away from each other, viewed somewhat from below. FIG. 3D is a cross-section as indicated.

FIG. 4 is a graph showing wear as a function of surface roughness.

FIG. 5A is a three-dimensional view of certain internal components such as the liner, the piston, the piston return spring and the piston washer, with the liner being shown semi-transparent. FIG. 5B is a cross-section of FIG. 5A. FIGS. 5C and 5D are additional cross-sections. FIG. 5E is a close-up view of the piston, piston washer and piston return spring. FIG. 5F is a view of the piston washer, and FIG. 5G is a cross-section of FIG. 5F.

FIG. 6 is a sectional view of the osteotome showing in particular the blade holder.

FIG. 7A is a three-dimensional view of the blade holder showing the place for insertion of the blade. FIG. 7B is another three-dimensional view with the blade in the background. FIG. 7C is a three-dimensional view of one component of the blade holder. FIG. 7D is a cross-sectional view of the blade holder. FIG. 7E shows the two-piece split retainer.

FIG. 8A is a cross-section of the blade holder and blade, showing the plunger for retaining the blade. FIG. 8B is a three-dimensional view of the plunger. FIG. 8C is a three-dimensional view of the twist-cam. FIG. 8D is another three-dimensional view of the twist-cam from another vantage point. FIG. 8E is another three-dimensional view of the twist-cam from another vantage point, showing the camming internal surface.

FIGS. 9A-9C are various sectional views showing various gas flowpaths through the body of the osteotome. FIG. 9A shows a section through the midplane. FIG. 9B shows a section somewhat removed from the midplane in one direction. FIG. 9C shows a section somewhat removed from the midplane in the opposite direction.

FIGS. 10A-10E are various three-dimensional views of the Auto Valve Cam.

Figure 13A:
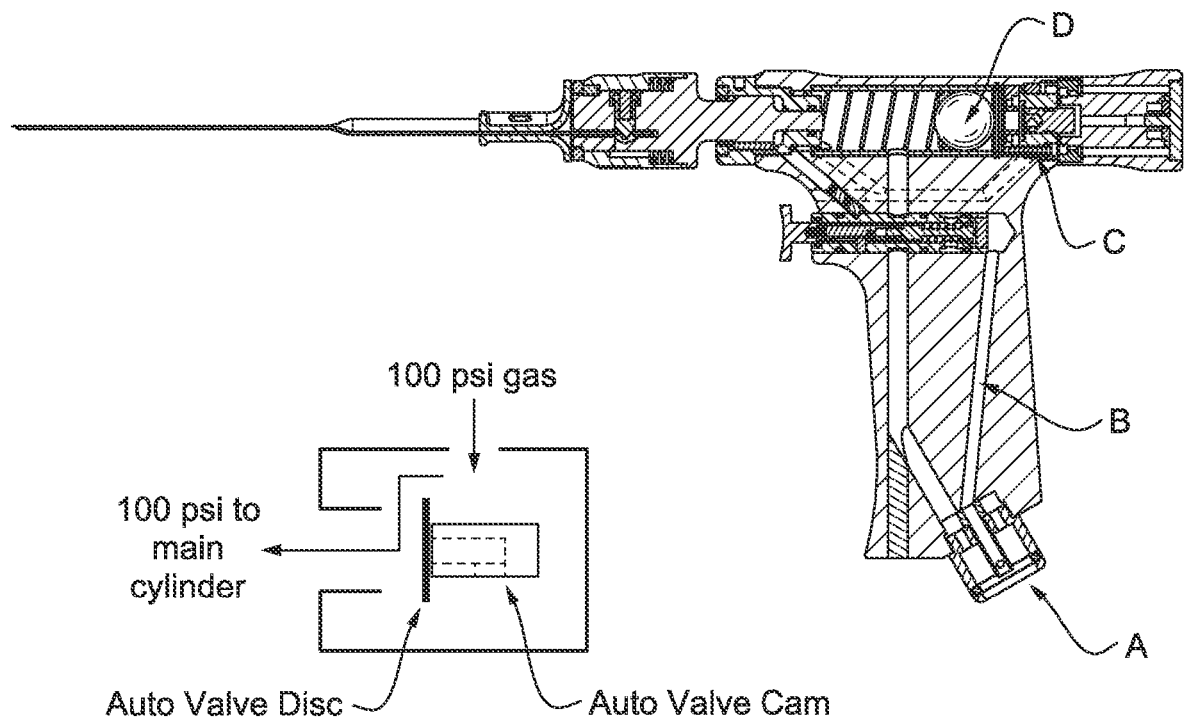
Figure 13B:
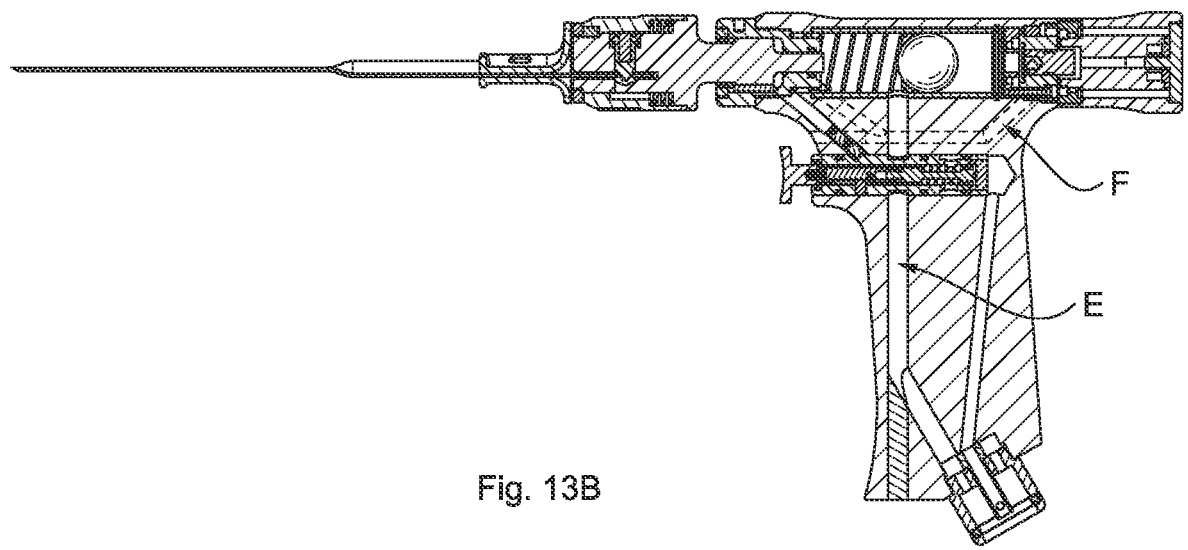
Figure 13C:
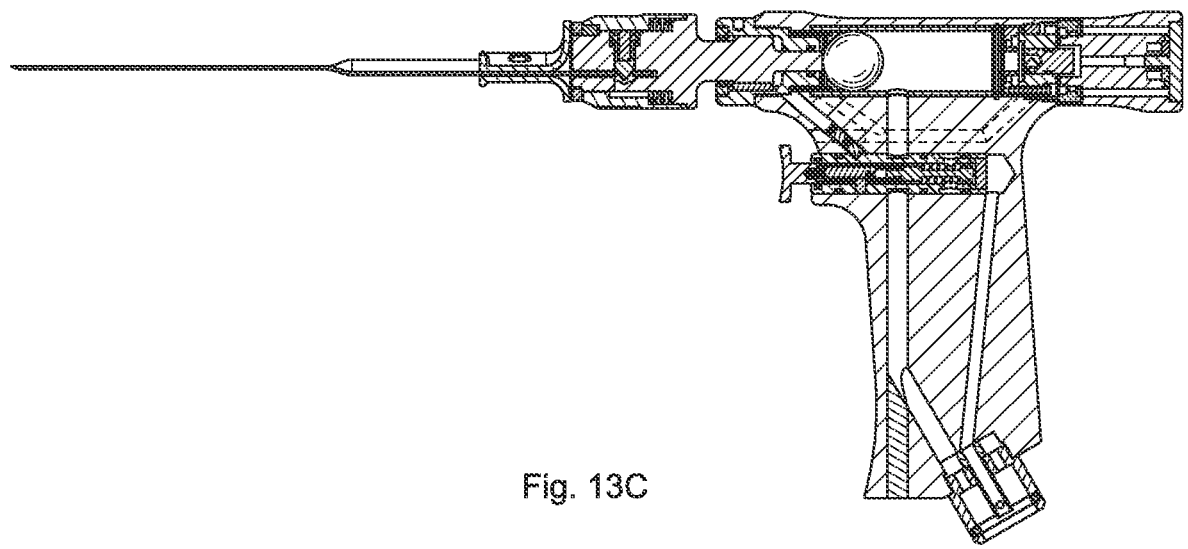
Figure 13D:
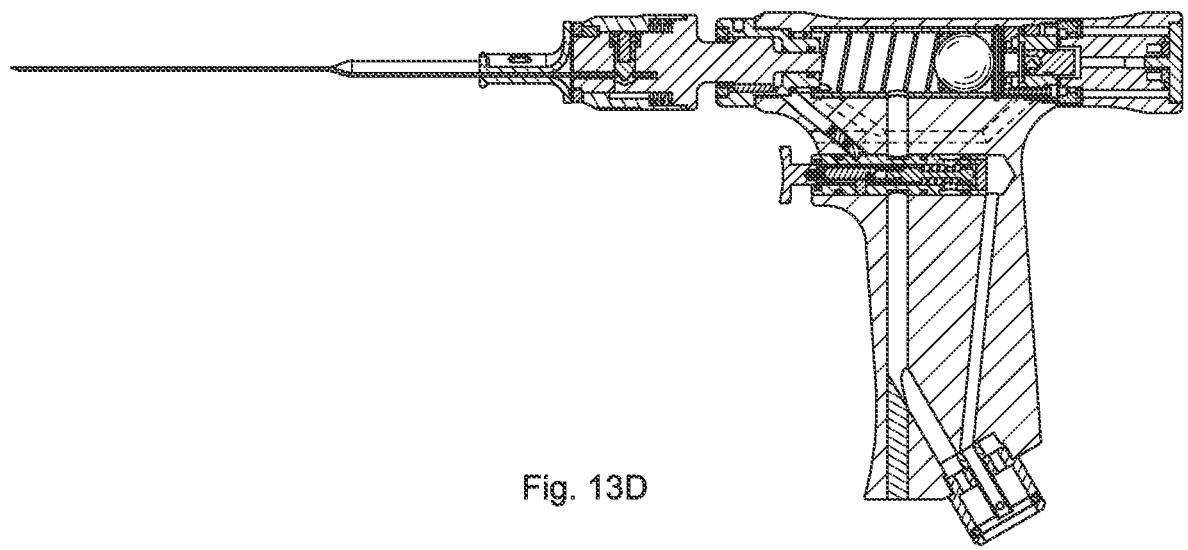

FIGS. 13A-13D show stages of operation relating to the single-stroke mode of operation. FIG. 13A, for single-stroke operation, shows the Auto Valve in a configuration in which Auto Valve Cam is in the retracted position. FIG. 13B shows the Auto Valve in a somewhat later stage of operation. FIG. 13C shows the Auto-Valve in a still later stage of operation. FIG. 13D shows the Auto-Valve in a still later stage of operation.

Figure 14A:
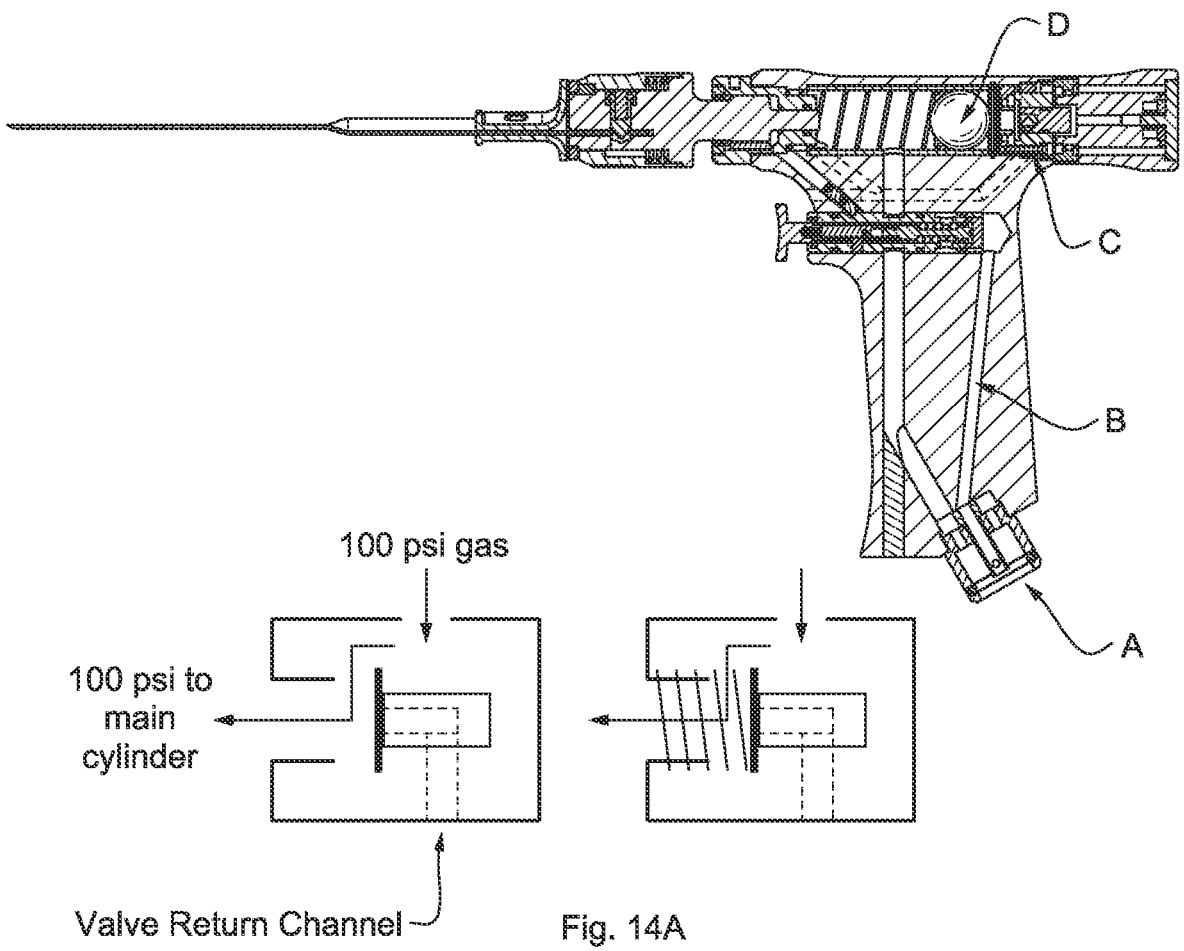
Figure 14B:
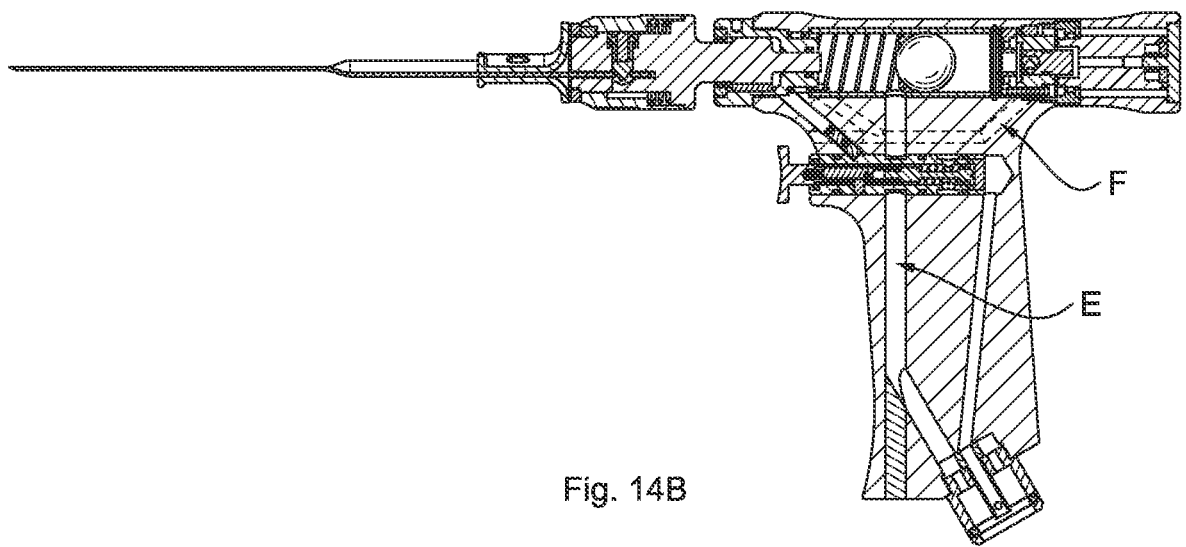
Figure 14C:
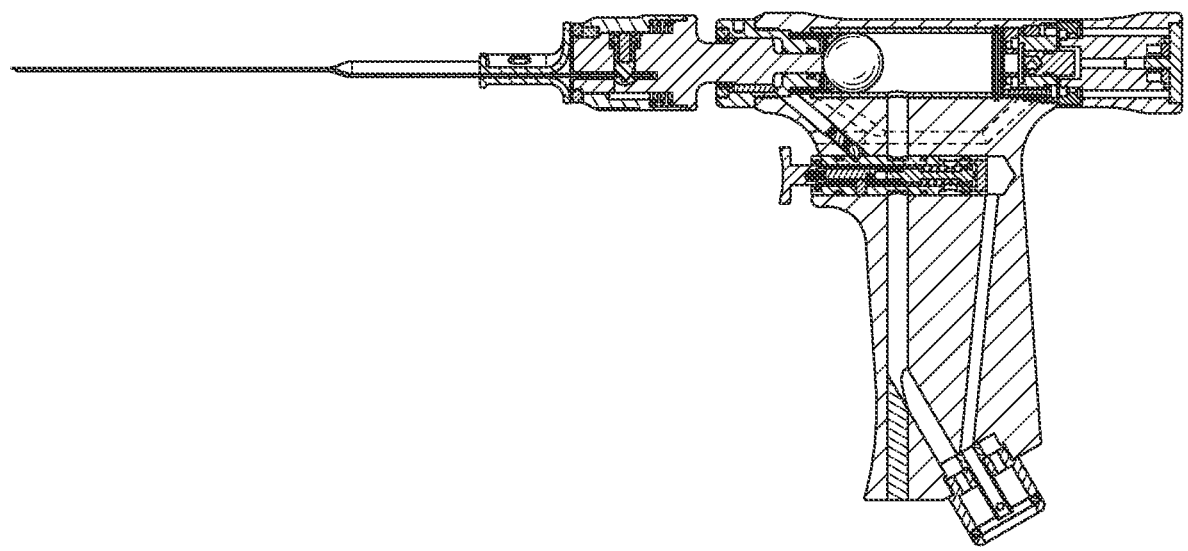
Figure 14C:
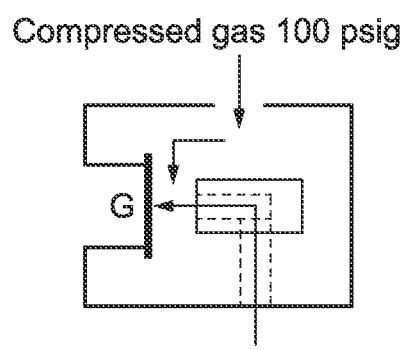
Figure 14C:
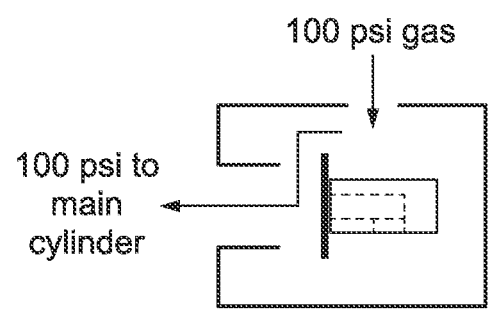

FIGS. 14A-14C show stages of operation relating to the multi-stroke mode of operation. FIG. 14A, for multi-stroke (repetitive) operation, shows the Auto Valve in a configuration in which the Auto Valve Cam is in the retracted position. FIG. 14B shows the Auto-Valve in a somewhat later stage of operation. FIG. 14C shows the Auto-Valve in a still later stage of operation.

DETAILED DESCRIPTION OF THE INVENTION

Referring now to FIGS. 1A-1I, in an embodiment of the invention, there may be provided a pneumatically powered osteotome 10 having an osteotome body. When viewed from the exterior, the osteotome 10, having a longitudinal direction 15, may generally comprise a handle region 20 and a piston region 30 that is connected to or integral with the handle region 20. The osteotome 10, including handle region 20 and piston region 30, may have an external shape and external dimensions such that it can be gripped by a hand of a user such as a surgeon.

In an embodiment of the invention, the osteotome may be capable of generating load on the blade 40 in a forward direction by impact of an impact piston on a surface of a blade holder, and may also be capable of transmitting load in a reverse direction to the blade 40. It also is possible, depending on the design of the osteotome, that the piston could directly impact the blade 40.

Blade

Figure 2A:
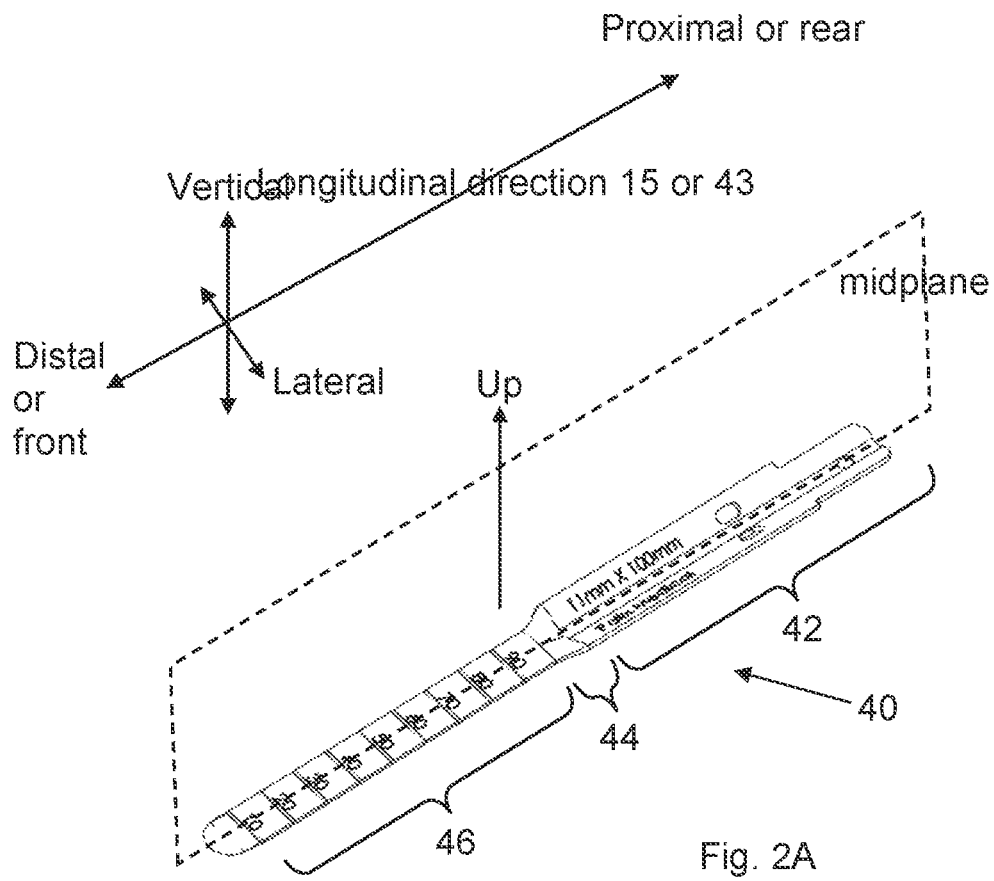
Figure 2B:
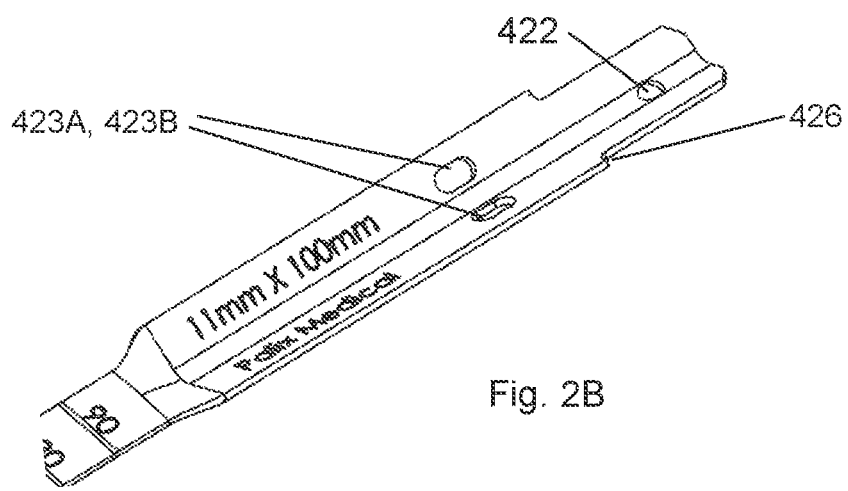

Embodiments of the invention can include a blade 40 for use with the osteotome. An embodiment of blade 40 is illustrated in FIGS. 2A-2B. Such a blade is described in U.S. Pat. No. 10,595,879.

Referring now to FIGS. 2A-2B, in embodiments of the invention, there may be provided a blade 40. The blade 40 may comprise, in sequence, a gripping portion 42, a transition portion 44, and a cutting portion 46. Blade 40 may have a longitudinal axis 43. Longitudinal axis 43 may extend along blade 40 in the direction from gripping portion 42 to transition portion 44 to cutting portion 46. Transition portion 44 is optional.

In an embodiment of the invention, blade 40 may have a three-dimensional shape but may be able to be stamped starting from a starting material that is planar, such as sheet metal.

The gripping portion 42 of the blade 40 may have therethrough a hole 422, or alternatively a slot (not illustrated). The gripping portion 42 may have a longitudinal axis 43, which may extend lengthwise along gripping portion 42, and which may lie in a plane of symmetry for at least some features of gripping portion 42. Hole 422 may be suitable to engage with another component of the osteotome 10 to help position or capture or restrain the blade 40 with respect to the blade holder or to apply force to the blade 40. The hole 422 may be located on the longitudinal axis 43 of gripping portion 42.

Blade 40 may further comprise a pair of slots 423A, 423B, which may be racetrack-shaped and may be elongated along the direction of griping region longitudinal axis 15. These slots 423A, 423B may serve to interact with a splash guard as described elsewhere herein.

The gripping portion 42 of the blade 40 may have a cross-section, in a plane that is perpendicular to the longitudinal axis 43, that is generally "V" with a rounded vertex of the "V" shape.

In addition, the gripping portion 42 of the blade 40 may further comprise a shoulder 426 such that the proximal portion of the gripping portion 42 may be narrower than the more distal portion of the gripping portion 42, transitioning at the shoulder 426. Shoulder 426 may be suitable for interaction with other components of osteotome 10 as described elsewhere herein. The transition between the wider portion of gripping region 42 and the narrower portion of gripping region 42 may comprise a surface that is generally perpendicular to the axis 15 of the gripping region 42 of the blade 40.

Blade designs other than what is illustrated here are also possible.

Splash Guard

Referring now to FIGS. 3A-3D, in an embodiment, blade 40 may be provided with a splash guard, which may comprise two pieces 9010, 9020 that loosely fit together with each other and with the blade 40 to divert droplets away from certain components of the osteotome 10. As illustrated, the splash guard may attach loosely to the blade 40, although other arrangements are also possible. The splash guard may comprise an upper piece 9010 and a lower piece 9020. Lower piece 9020 may have posts 9030 engageable with upper piece 9010.

Slots or holes 423A, 423B in the blade 40 may be located one in each arm of the "V" and may be located symmetrically with respect to each other around a central longitudinal plane of symmetry. Such slots or holes may be suitable to engage with the splash guard, more specifically with posts 9030. Slots or holes 423A, 423B are illustrated as being racetrack-shaped, although other shapes are possible. Slots or holes 423A, 423B are illustrated as being generally perpendicular to the local flat surfaces of the "V" shape. However, it is alternatively possible that such slots or holes could be aligned in the vertical direction of the blade 40, or could have still other orientation as may be desired.

Cylinder Liner

Referring now to FIG. 1D and FIGS. 5A-5G, the osteotome 10 may comprise piston region 30, which may have therewithin a cylindrical space which may be defined by a cylinder liner 50. Cylinder liner 50 may be a separate piece from the rest of the body of osteotome 10, and may be made of a material that is different from the material of the rest of the body of osteotome 10. Cylinder liner 50 may be inserted into and may be adhered to the rest of the body of osteotome 10. The cylinder liner 50 may have a wall thickness of at least 0.010 inch. Cylinder liner 50 may have therein an axial bore that may be generally cylindrical and that may have an internal diameter that is substantially constant along its length. Cylinder liner 50 may have a longitudinal axis 52 that is an axis of rotation defining the internal surface of cylinder liner 50.

Cylinder liner 50 may comprise or may be made of a low-friction material. For example, the material for cylinder liner 50 may have a coefficient of dynamic sliding friction, measured against the material of which the spherical piston 100 is made, that is less than 0.20, or less than 0.10, or less than 0.05. Also, or alternatively, the material for cylinder liner 50 may have a coefficient of dynamic sliding friction, measured against itself, that is less than 0.20, or less than 0.10, or less than 0.05. For example, the material for cylinder liner 50 may be a polymeric material. More specifically, the material may be a fluoropolymer such as any known form of polytetrafluoroethylene, commonly known as Teflon™, such as the commercially available Rulon®. Other possible materials include polyetheretherketone (PEEK), and Ultra High Molecular Weight Polyethylene (UHMWPE). Non-polymeric materials such as ceramics or metals are also possible. The term fluoropolymer is intended to include fluoropolymers that are "filled" with particles of another material. Cylinder liner 50, alternatively, may comprise or may be made of a metal still other materials. Cylinder liner 50 may have, on its internal surface, a surface finish of 125 microinches rms or smoother. It is believed, although it is not wished to be limited to this explanation, that constructing the cylinder liner 50 of a material that has such a low coefficient of sliding friction provides significant benefit in improving the reliability of the device.

In an embodiment of the invention, the fluoropolymer may be a fluoropolymer that is "filled" with particles of another material. The additional material may be of a nature that in some way modifies or improves the wear or friction properties of the basic polymer material, or changes the coefficient of thermal expansion of the basic polymer material. Typical materials for filler are glass fibers, bronze particles, graphite particles, polyimide particles, and aluminum particles.

It can be noted that, as is visible in FIG. 5B, it is possible for there to be sideways holes through the liner 50 to permit the passage of gas therethrough. Liner 50 is shown semi-transparent in FIGS. 5A and 5B. In FIGS. 5C and 5D, liner 50 and other components are shown sectioned in two different planes.

Spherical Piston

Figure 1A:
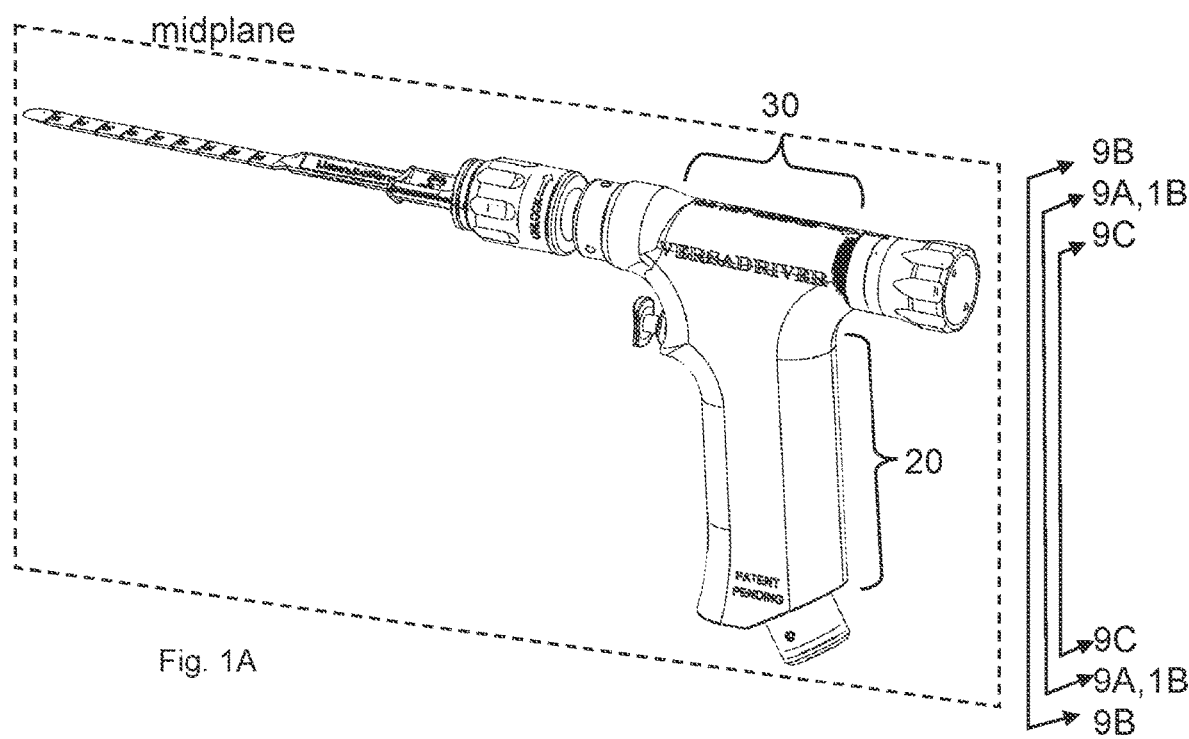
Figure 1B:
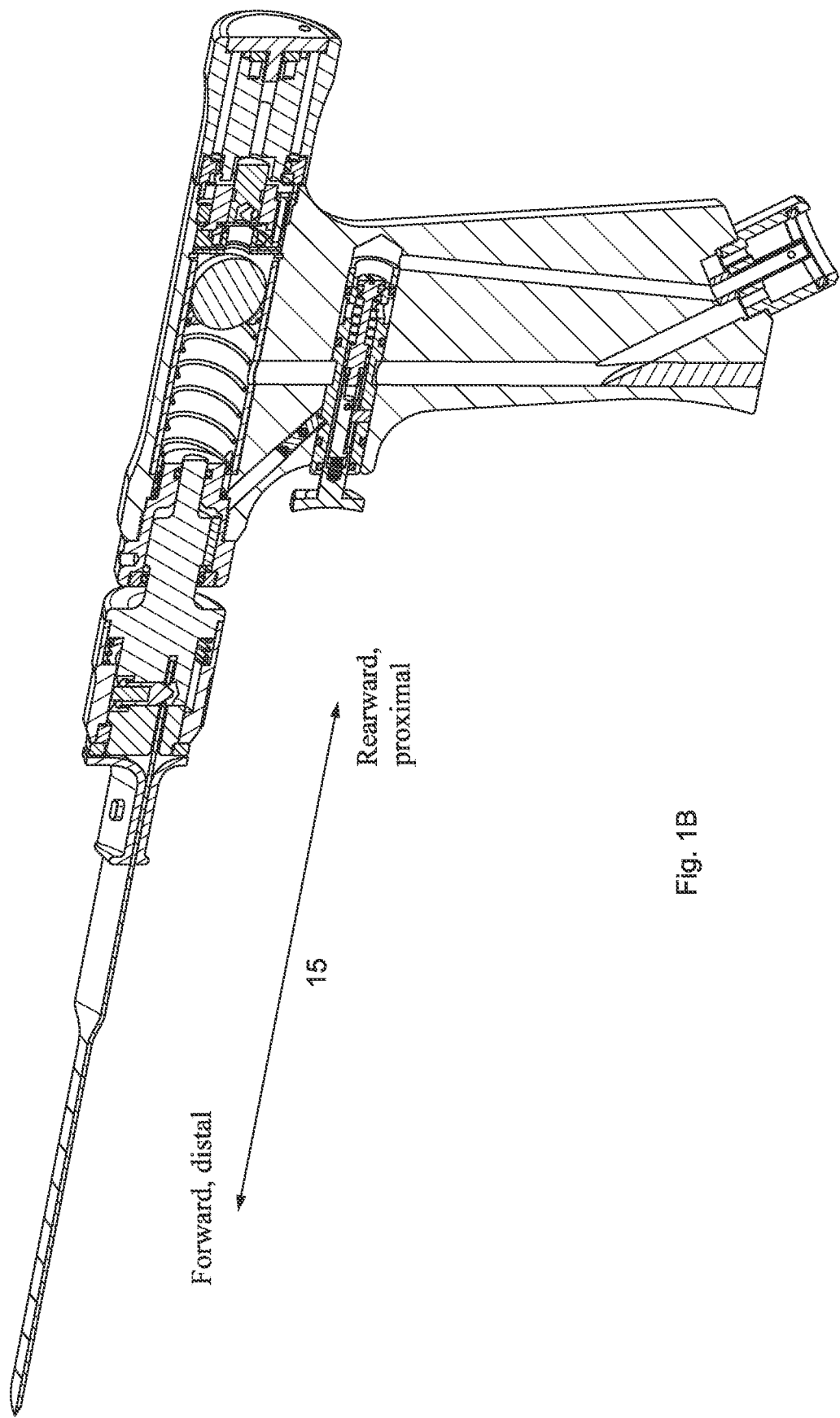
Figure 1C:
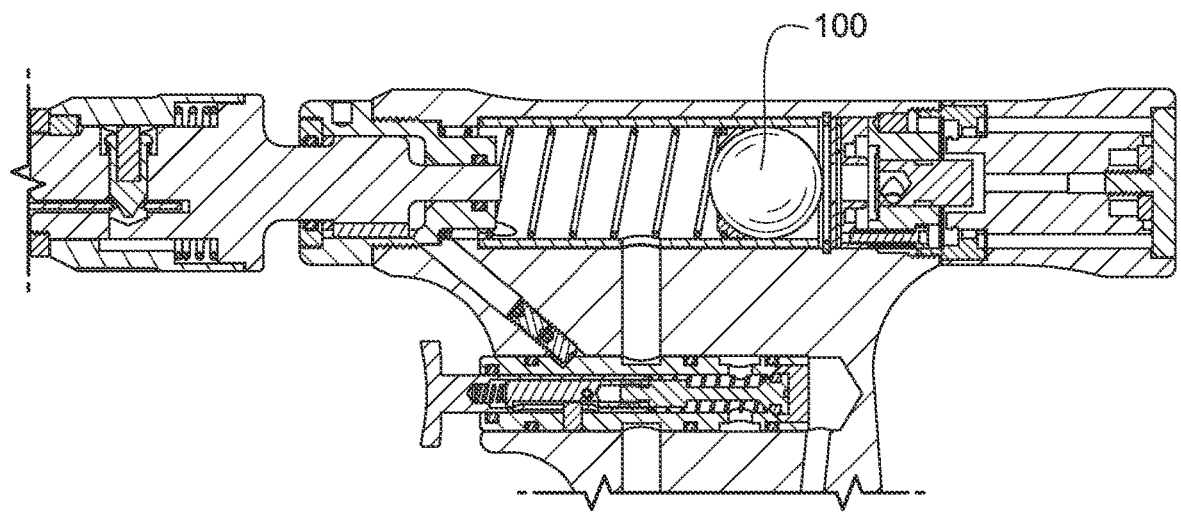
Figure 1D:
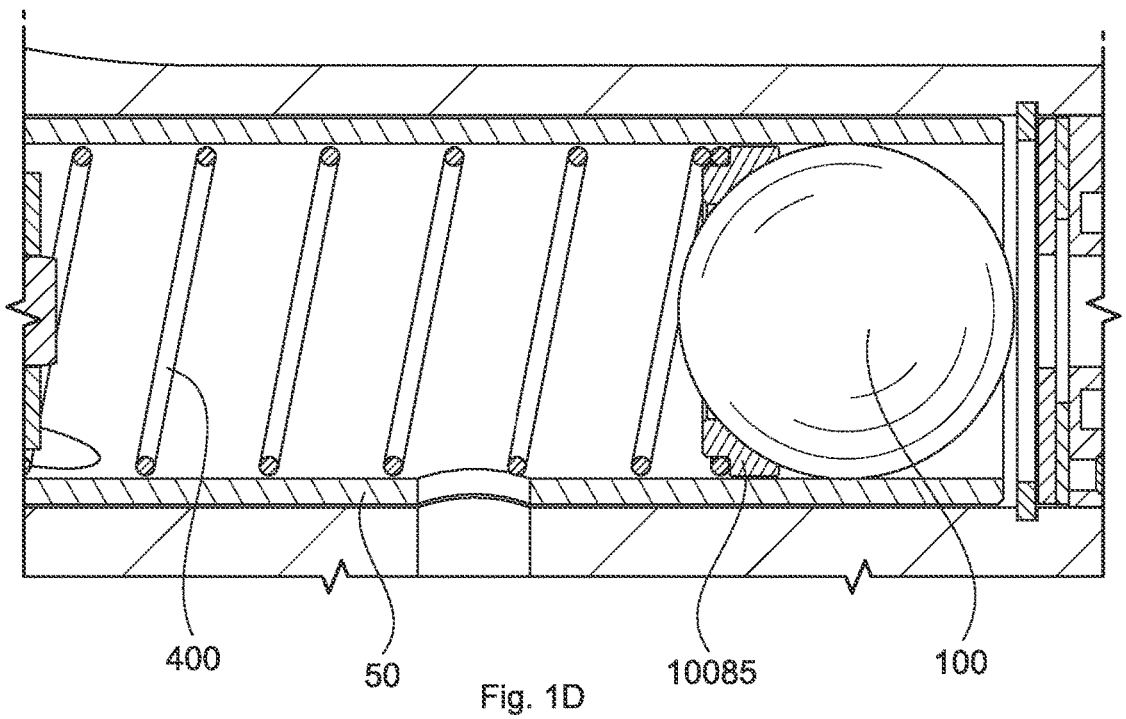
Figure 1F:
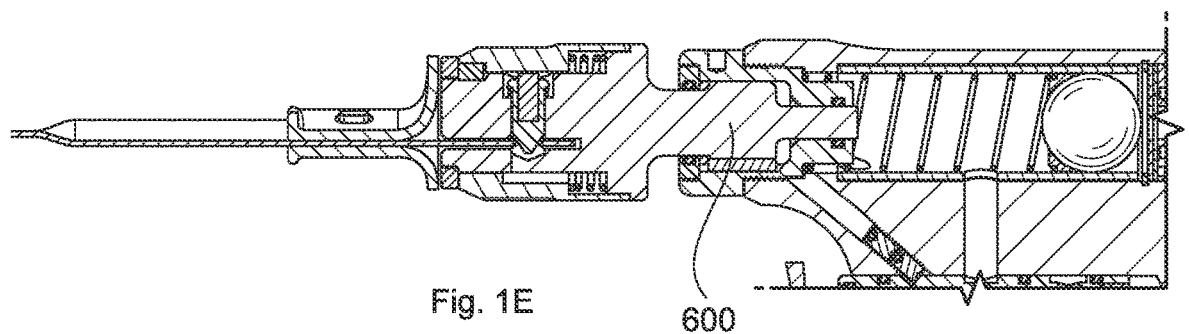
Figure 1F:
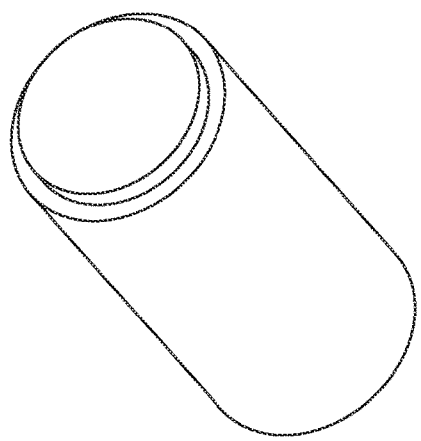
Figure 1G:
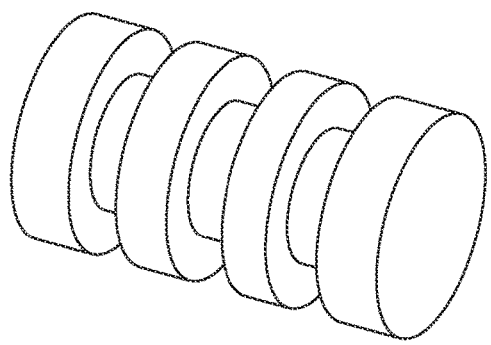
Figure 1H:
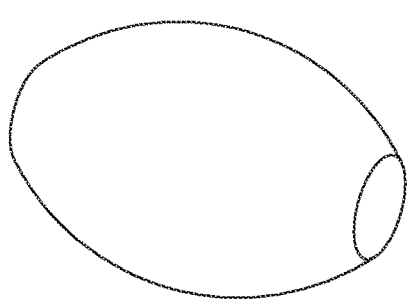
Figure 1I:
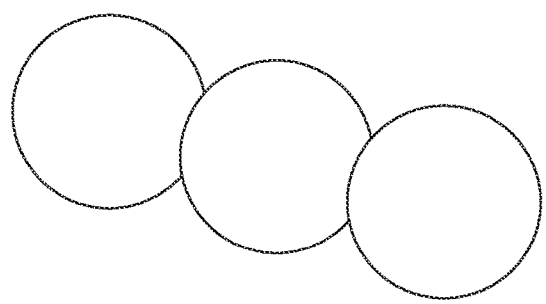

With continued reference to FIGS. 1C-1E and with reference to FIGS. 5A-5G, there may further be provided a spherical piston 100 that is contained within cylinder liner 50 and is movable within the cylinder liner 50 along the longitudinal axis 52 of the cylinder liner 50.

In an embodiment of the invention, spherical piston 100 may be free to rotate or spin around any of its axes as it executes any translational or other motion with respect to cylinder liner 50. This freedom for rotation and spinning encourages a variety of locations on the surface of spherical piston 100 to interact with other components such as cylinder liner 50. It can be expected that the choice of what point(s) on the surface of spherical piston 100 are interacting with other components such as the internal surface of cylindrical liner 50 at any given time will be somewhat random, and will change over time. It can be expected that eventually the entire surface of spherical piston 100 will experience such interaction. Similarly, it can be expected that the locations on cylindrical liner 50 that are touched by spherical piston 100 would vary as a function of time in a random manner. This encourages that contact and wear should be generally uniformly distributed on both the cylinder liner 50 and the spherical piston 100. Because, in embodiments, the cylinder liner 50 is softer than the spherical piston 100, it can be expected that wear occurs preferentially on the softer material of the cylinder liner 50.

The spherical piston 100 may be made of or may comprise a material having a hardness of at least Rockwell C70 or C65. Such material may be tungsten carbide or other suitable material. However, it is also possible to use pistons that are not so hard, such as Rockwell C45. In an embodiment of the invention, spherical piston 100 may have a diameter of 0.750 inch and may have a surface roughness of 8 micro inches rms or smoother. More generally, the spherical piston 100 may have a diameter in the range of between 0.50 inch and 1.50 inches. Such spheres are commercially available made of tungsten carbide with a diametral tolerance of +/−0.0001 inch, and with a hardness of Rockwell C75.

If the diameter of the spherical piston 100 is 0.75+/−0.0001 inch, then the inside diameter of the cylinder liner 50, for example, may be chosen to be 0.7505+0.0010/−0.0000 inch. The clearance (diametral) resulting from these combinations of dimensions can range from 0.0004 inch to 0.0016 inch. More generally, the diametral clearance can range from 0.0001 inch to 0.005 inch, or from 0.0001 inch to 0.010 inch.

It is found, perhaps surprisingly, that there is an optimum roughness for the surface of the spherical piston 100. It is understandable that an excessively rough surface of the spherical piston 100 is undesirable because it could gouge the internal surface of the cylinder liner 50. However, an extremely smooth surface of spherical piston 100 is also not desirable. The reason for not wanting the surface finish of the spherical piston 100 to be too smooth is that this actually increases wear on the cylinder liner 50. It is believed that a slight roughness of the surface of the spherical piston 100 has the result that the surface of an optimally rough spherical piston 100 creates a small amount of dust particles of the material of the cylinder liner 50 (such as Rulon) so that the resulting dust particles fill in and stay in and smooth out the surface of the spherical piston 100, resulting in a very thin uniform coating of Rulon dust on the spherical piston 100. This creates the situation of Rulon rubbing against Rulon as the spherical piston 100 operates, and this situation creates very low friction.

This phenomenon is believed to be important for self-lubricating and dry-running polymers, and is referred to as a transfer film layer. it is believed to be important that a transfer film can form on the surface of the spherical piston 100. Otherwise, the polymer of cylinder liner 50 could become more and more abraded during use. It is believed that this protective transfer film reduces the wear actions by filling the protruding roughness peaks and valleys of the part on which the transfer film is deposited. Transfer films are formed by wear debris of the bearing material depositing onto the harder material. Transfer films are very thin structures having a thickness typically smaller than 1 μm.

It is also believed that if the material such as the material of spherical piston 100 is too smooth, it will not generate a transfer film and therefore the mating parts such as the cylinder liner 50 will actually experience much greater wear than would occur with the existence of a material with an appropriately rough finish appropriate to create a transfer layer.

Figure 4:
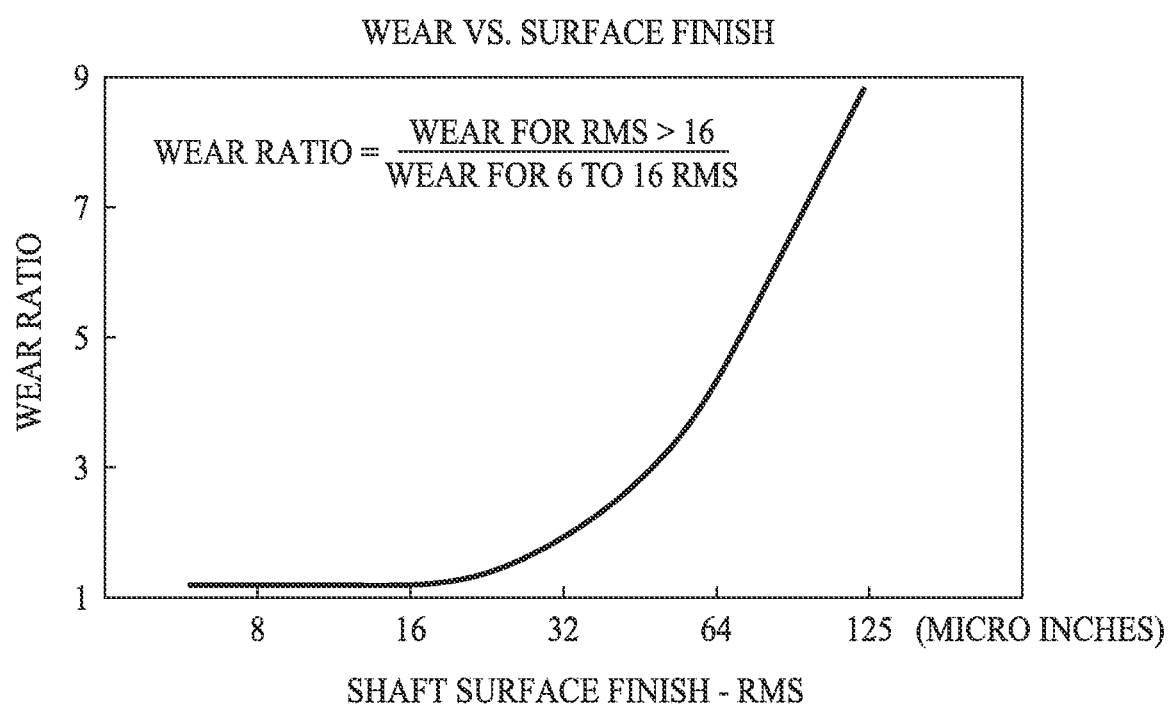
Figure 5F:
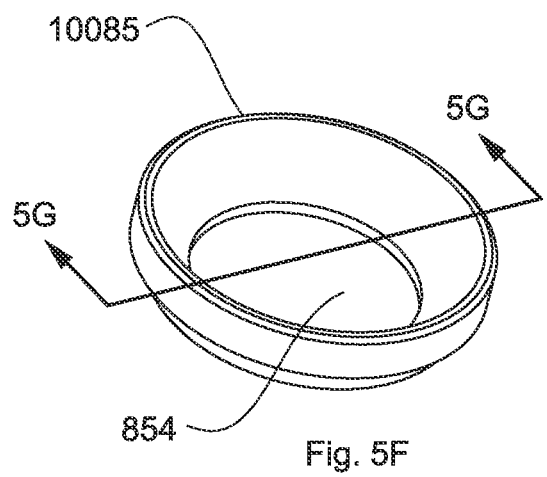
Figure 5G:
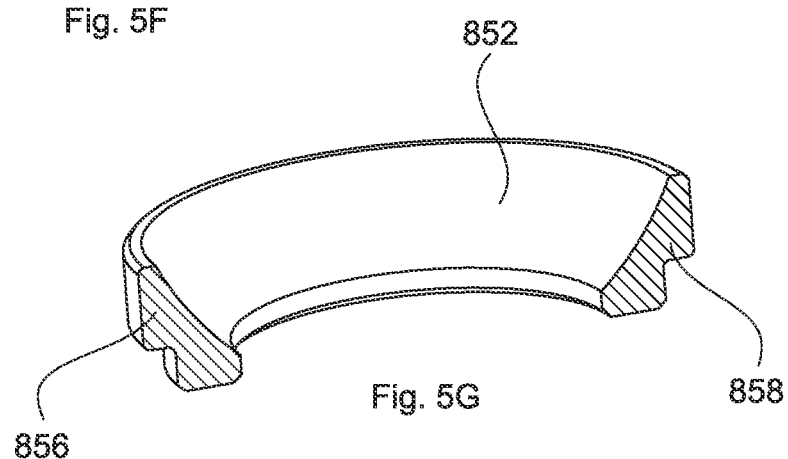

FIG. 4 is a graph that illustrates relative wear. The vertical axis is the wear at a given roughness (microinches rms), divided by the wear that is experienced at a surface roughness of 6 to 16 microinches rms. It is believed that a surface roughness of 6 to 16 microinches rms is optimal. It is found that for larger roughnesses the wear increases, as shown by the ratio plotted in FIG. 4 being larger than 1. It is believed that the optimum surface finish for the spherical piston 100 is between 6 and 16 microinches rms (root-mean-square) having a texturing that is randomly oriented. It is believed that if the surface of spherical piston 100 is rougher than this range, the wear of cylinder liner 50 will increase significantly. It is also believed that if the surface of spherical piston 100 is smoother than this, a transfer film may not form, and the lack of a transfer film would also increase the wear of cylinder liner 50. In embodiments, the roughness may be specified as between 5 and 20 microinches rms, or, more generally, between 4 and 32 microinches rms. The randomness of the texture of the surface of spherical piston 100 means the that the surface presents itself as many randomly oriented peaks and valleys as opposed to a directional texture that would look like a series of waves generally aligned in a particular direction. The surface of the PTFE material, when engaged with the piston surface of random peaks and valleys, will have a tendency to move or flow around the peaks without excessive shear stress and resultant wear. In the contrasting situation where the PTFE surface encounters directional textured surfaces, the PTFE will likely have a tendency to plow over the peaks creating high stress on the material surface resulting in higher friction and greater wear. It is therefore believed to be advantageous to have a randomness to the texture of the surface of spherical piston 100. This can be achieved with orbital or multi-directional sanding of the surface of spherical piston 100 or with diamond sandpaper.

Polytetrafluoroethylene (PTFE) materials are sometimes "filled," that is, combined with other materials to obtain certain characteristics that PTFE by itself cannot offer. Common examples of such filler materials are glass fibers, bronze particles, graphite particles, polyimide particles, and aluminum particles. The amount and size of the particles or fibers can be varied to achieve the specific properties sought. Among the characteristics that can be altered are creep resistance, wear resistance, thermal expansion, and pressure loading. We have found that a PTFE filled with 15% glass fiber is excellent for our application.

Although a spherical piston 100 is described and illustrated in detail herein, it also is possible to use other shapes of piston. Alternative shapes of piston are illustrated in FIG. 1. For example, the piston could be generally cylindrical, or cylindrical with steps in it. It also is possible that the piston could be of an ellipsoidal shape, which could ne truncated. It also is possible that the piston could be more than one sphere, which may be joined to each other.

Piston Return Spring

With continued reference to FIGS. 1B-1E and with reference to FIGS. 5A-5G, there may also be provided a piston return spring 400, which may be a helical compression spring, which may occupy space inside cylinder liner 50. Spring 400 may be deformable between an extended configuration and a collapsed configuration. In its extended configuration, spring 400 may urge spherical piston 100 to an extreme rearward position (rightward in the orientation illustrated in FIGS. 1B-1E) in which spherical piston 100 touches against a rearward end or stop of the Main Cylinder. In its collapsed configuration, spring 400 may allow spherical piston 100 to travel to an extreme forward (left as illustrated) position in which spherical piston 100 touches a rearward-facing surface of blade holder 600. Spring 400 may occupy an envelope that is generally cylindrical and may have an outside diameter that is between approximately 80% and approximately 98% of the inside diameter of cylinder liner 50. Spring 400 may be made of or may comprise a suitable metal such as stainless steel.

Some of spring 400 may be located in an annular space between the rearward portion of blade holder 600 and cylinder liner 50. The annular space may be dimensioned, along the axial direction, such that spring 400 can compress sufficiently to allow spherical piston 100 to touch blade holder 600 for any permitted position of blade holder 600.

Piston Washer

Referring now to FIGS. 5A-5G, there may also be provided a piston washer 10085. Washer 10085 may have a concave cup-shaped depression 852 on its surface that faces spherical piston 100. The depression 852 may have a spherical radius that is substantially identical to the radius of spherical piston 100, or slightly greater than the radius of spherical piston 100, so that spherical piston 100 can easily occupy depression 852 and will act to keep washer 10085 centered with respect to cylinder liner 50. Alternatively, it is also possible that depression 852 in washer 10085 could have other shapes that are receptive for spherical piston 100. There are also other possibilities for the relationship between spherical piston 100 and depression 852. Washer 10085 may be axisymmetric.

Washer 10085 may have therethrough a central opening 854, such that when spherical piston 100 is seated in depression 852 in washer 10085, spherical piston 100 protrudes through central opening 854 and extends beyond washer 10085 suitably to directly impact or contact a next component without washer 10085 having to contact the next component. The next component can be blade holder 600, which can also be referred to as force-transmitting component, as described elsewhere herein. Another possibility is that even if spherical piston 100 does not protrude through central opening 854 and extend beyond washer 10085, if there is appropriate local geometry of the force-transmitting component such as a blade holder 600, or of the blade 40 itself, it is still possible for spherical piston 100 to contact and transmit force to the force-transmitting component (blade holder 600). As yet another alternative, it is also possible that the piston could contact the blade 40 directly and transfer force directly to the blade 40.

Washer 10085 may have a head region 856 and a neck region 858, the head region 856 being larger in transverse dimension (transverse to the longitudinal axis of cylinder liner 50) than the neck region 858. The head region 856 may have an outside diameter that is between approximately 80% and approximately 98% of the inside diameter of cylinder liner 50. The head region 856 could have a transverse dimension that is smaller than the diameter of spherical piston 100. As a result, piston washer 10085 could have a larger gap with respect to cylinder liner 50 than the gap between spherical piston 100 and cylinder liner 50. Head region 856 may, as illustrated, be cylindrical, or it alternatively could be rounded at its exterior in multiple directions such as ellipsoidal or may have some other edge shape that is rounded in a sectioning plane that contains said longitudinal axis. The outside diameter of the head region 856 of washer 10085 may be larger than the outside diameter of the envelope of spring 400.

Washer 10085 may also have a neck region 858, connected to or integral with head region 856, and facing away from spherical piston 100. Neck region 858 may be able to fit between inside diameter of coils of spring 400, and neck region 858 of washer 10085 may serve to maintain spring 400 centered inside cylinder liner 50. When the outside diameter of neck region 858 is compared to the dimensions of the coils of spring 400 in the absence of washer 10085, the relationship may be such that neck region 858 of washer 10085 may require the coil of spring 400 to expand somewhat in order to receive neck region 858, and so there may be a sort of interference fit between the neck region 858 and the coil of the spring 400. It is possible that the neck region 858 could have an outside diameter that is greater than an inside diameter of the coil of the piston return spring in an undeformed condition, but the neck region 858 can fit inside the coil of the piston return spring when the coil is deformed radially outward, such that the coil in the radially-outward-deformed condition still has a smaller outside diameter than an outside diameter of the head region, and so gouging of the liner 50 still can be avoided.

As yet another alternative, it is possible that spherical piston 100 could transmit force to washer 10085 which in turn transmits force to blade holder 600 or to blade 40 directly. Other shapes of washer 10085 are also possible.

The washer 10085 may be made of a metal such as titanium or aluminum or stainless steel. It would also be possible to use other materials that are sufficiently strong and tough.

In general, the described design and construction and interrelationship of washer 10085 with other components may prevent the spherical shape of the spherical piston 100 from exerting radially outward forces on the coil or wire of spring 400 during compression of spring 400. In the absence of washer 10085, such radial forces caused by the piston 100, if allowed to occur, could tend to expand the spring 400 sufficiently to cause spring 400 to contact the internal wall of the cylinder liner 50. Such contact could cause undesirable wear as the spring 400 pushes against the cylinder liner 50, and could even create a gouge in the internal surface of cylinder liner 50. This problem has been known to occur in prior art osteotomes. This problem could result in wear and even dust, which could cause parts to seize. It is also true that any enlarging of the clearance between the spherical piston 100 and the cylinder liner 50, such as due to gouging or wear, could enlarge the clearance gap between the spherical piston 100 and the cylinder liner 50, which would increase leakage of gas between the spherical piston 100 and the cylindrical liner 50, which could reduce the amount of impact force deliverable by the osteotome 10. This spreading-out of piston return spring 400, and possible gouging or wear, could be a problem if the cylinder liner 50 is made of a material that is soft, such as various low-friction polymers. In contrast, with the use of washer 10085, it is possible that such radially-outward spreading force caused by the piston will not occur. It is also possible, as described herein, that some spreading-out of the coil could be caused by neck region 858 of washer 10085, but the amount of such spreading is a defined amount that is insufficient to cause wear or gouging.

At the opposite end of spring 400, there may be a relationship between inside diameter of coils of spring 400 and the outside diameter of the appropriate portion of blade holder 600 so as to keep that end of the spring 400 centered inside cylinder liner 50.

Blade Holder Overall Features

Figure 6:
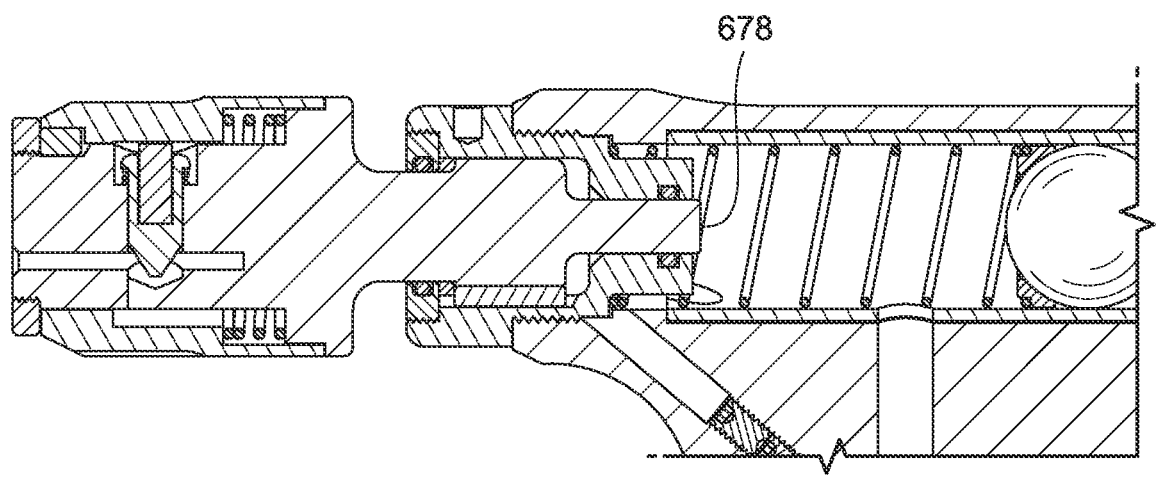
Figure 7A:
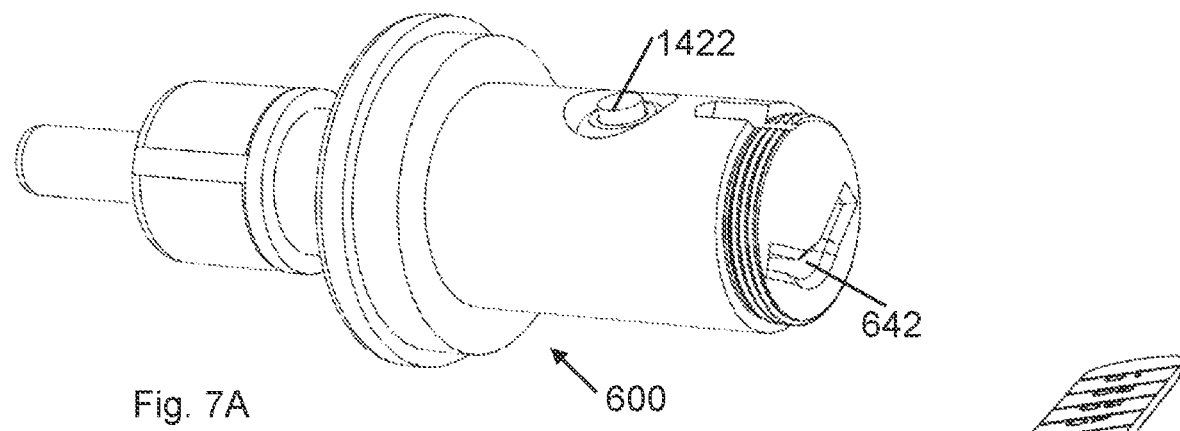
Figure 7B:
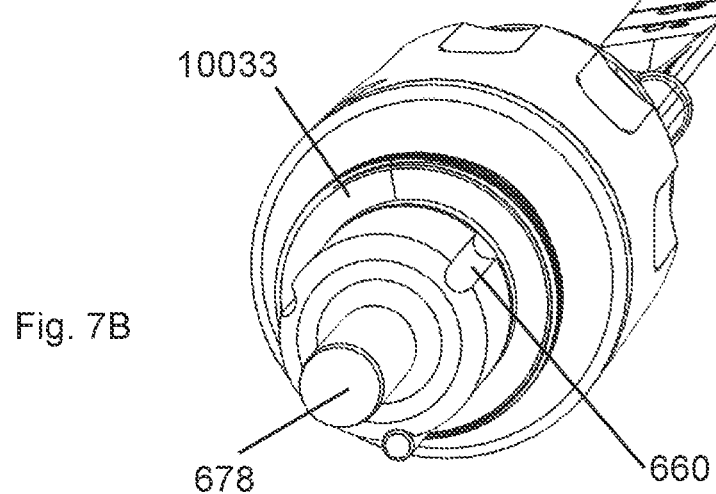
Figure 7C:
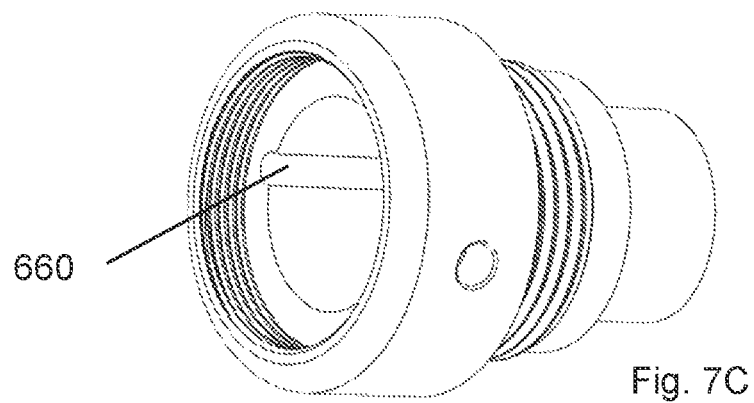
Figure 7D:
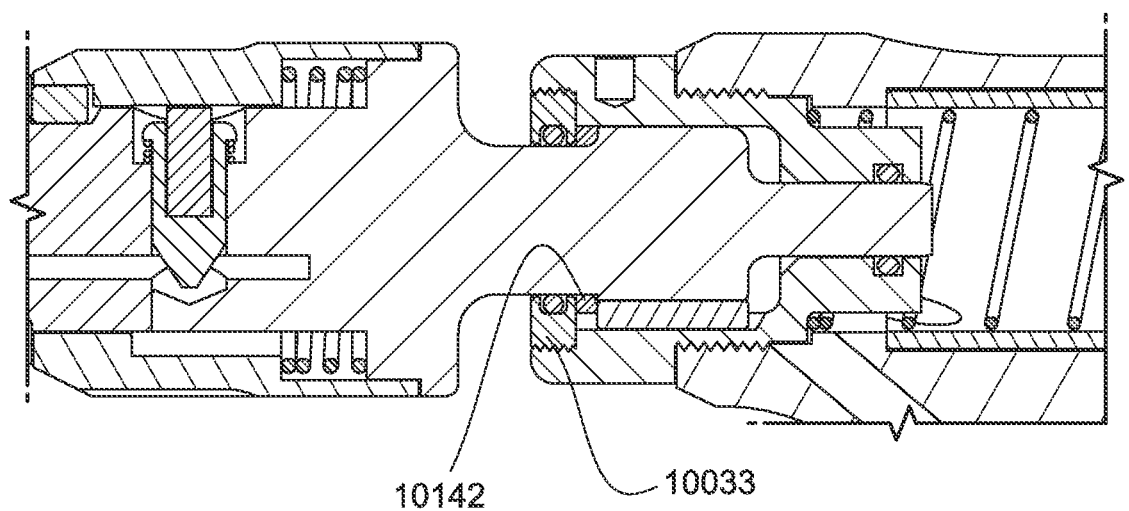
Figure 7E:
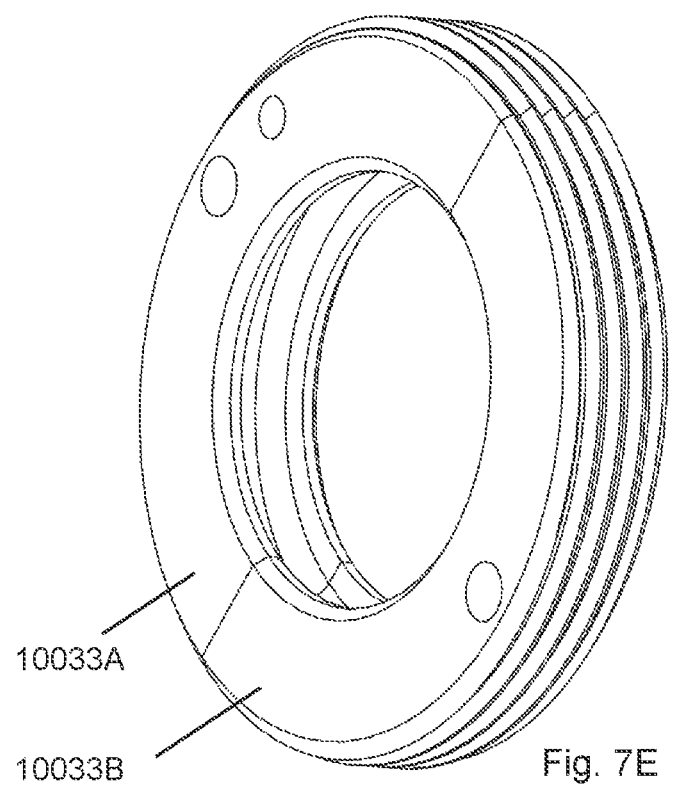

Referring now to FIG. 6, blade holder 600 may have certain overall features. Blade holder 600 may, at a rearward end, be disposed and designed suitably to be impacted by spherical piston 100, such as at surface 678, during an appropriate portion of the stroke of spherical piston 100. At its forward end, blade holder 600 may be suitable to receive a blade 40 and to hold blade 40 and to transmit force to blade 40. Blade holder 600 may have a movable relationship to a body of osteotome 10 such that blade holder 600 is guided in translational motion with respect to a body of osteotome 10.

In an embodiment of the invention, blade holder 600 may be axisymmetric in many of its external features. In an embodiment of the invention, the guiding of translational motion of blade holder 600 can occur by a piston-cylinder relationship.

Blade Holder Exterior and More Rearward Features of Blade Holder

Referring now to FIG. 6 and FIGS. 7A-7E, blade holder 600 may comprise a generally cylindrical piston that rides inside a cylinder that is part of osteotome 10. Such piston-cylinder relationship may provide guidance and constraint for the motion of blade holder 600 allowing the blade holder 600 to translate forward and backward along the axis of the blade holder 600.

As illustrated in FIG. 6, there may be provided two different piston-cylinder relationships involving blade holder 600 and the body of osteotome 10, at two different axial locations and having different diametral dimensions. As illustrated, the two different piston-cylinder arrangements are coaxial with each other. Blade holder 600 may comprise a larger-diameter generally cylindrical region that is in close-fitting relationship with a larger cylinder and is more forward-located. Also, blade holder 600 may have a rearward extension that is a smaller-diameter generally cylindrical region that is in close-fitting relationship with a smaller cylinder. The larger-diameter generally cylindrical region may be coaxial with the smaller-diameter generally-cylindrical region, and the larger cylinder may be coaxial with the smaller cylinder, and all of them may be coaxial with each other. O-rings or similar seals may be provided at or near either or both of these piston-cylinder relationships.

In general, the portion of blade holder 600 that is involved in transferring load from the impact of spherical piston 100 to the blade 40 may be of single-piece construction to the greatest extent possible. This is believed to improve reliability. For example, this is seen in the embodiment in which the blade 40 resides in a blade-shaped slot 642 that is present in a blade holder 600 that otherwise is substantially solid in the region where the gripping region 42 of blade 40 overlaps (in the axial direction) with the blade holder 600. Clamping of the gripping region 42 of blade 40 is accomplished by the plunger (described elsewhere herein) rather than by split or separate pieces of blade holder 600 in the vicinity of gripping region 42.

Blade holder 600 may be provided with an anti-rotation feature so that blade holder 600 is constrained against rotation around its own axis. As illustrated, the anti-rotation feature may take the form of a cutaway 660 in the outer perimeter of the larger-diameter generally cylindrical region of blade holder 600. The cutaway 660 may extend along the axis of the blade holder 600 and may be hemi-cylindrical. In the corresponding part of the corresponding cylinder, there may be another cutaway which also may be hemicylindrical. The paired hemicylindrical cutaways may be occupied by a generally cylindrical pin with sufficient clearance to allow sliding along the length of the pin. As illustrated, three sets of such cutaways 660 are provided in the blade holder 600, distributed at equiangular intervals of 120 degrees. In order to achieve angular constraint, it is sufficient for one pin to be provided in one cutaway 660. In general, with three sets of cutaways, three angular orientations of blade holder 40 are possible, but in practice the illustrated orientation is likely to be preferred. It is possible to provide multiple slots or cutaways 660 in the blade holder 600 and it is possible that the pin could be such that it could be temporarily taken out of position so the blade holder 600 could be rotated and then the pin reinserted to make an indexable rotary blade holder.

This could be beneficial in positioning the blade edge at the most appropriate angle relative to the hand of the surgeon gripping the handpiece.

The presence of two piston-cylinder relationships along the blade holder 600 helps to provide good definition of the translational path of the blade holder 600.

Retaining Collar and Resilient Material

Referring now to FIGS. 7A-7E, near the forward end of the body of osteotome 10 exclusive of the blade holder 600, there may be provided a retaining collar 10033 such that in the absence of retaining collar 10033 it is possible to insert and remove blade holder 600 into osteotome 10 from the front of the osteotome 10, while in the presence of retaining collar 10033 it is not possible to remove blade holder 600 from osteotome 10. Retaining collar 10033 may be disc-shaped and may be threaded on its exterior to correspond with another thread in a receiving component of osteotome 10. Retaining collar 10033 may have an inside diameter that is smaller than a corresponding dimension of a portion of the blade holder 600 so as to retain the blade holder 600. In the illustrated embodiment, retaining collar 10033 is split in two pieces 10033A, 10033B and is assembled onto the shaft of the blade holder 600 and then both parts 10033A, 10033B together are screwed into the receiving component as described elsewhere herein.

Furthermore, osteotome 10 may comprise a resilient material 10142 which may be positioned between a forward-facing surface of the blade holder 600 and a rearward-facing surface of the retaining collar 10033. The resilient material 10142 may be suitable to be compressed to absorb some forward motion of the blade holder 600 and also may be suitable to expand to urge the blade holder 600 in a rearward direction when there is not a forward-directed force being applied to the blade holder 600 or to the resilient material 10142.

It can be understood that, in an embodiment of the invention, the retaining collar 10033 provides a stop that resists or limits the forward motion of the blade holder 600. Just rearward of the retaining collar 10033 may be a resilient material 10142 that participates in the load path for transfer of load from the blade holder 600 to retaining collar 10033. As discussed elsewhere herein, it may be desirable to have the blade holder 600 be substantially one-piece construction as much as possible. However, in embodiments the blade holder 600 forward of the retaining collar 10033 has a substantially large outer dimensions, larger than the retaining collar 10033. Also, rearward of the retaining collar 10033 there may be a piston whose outside diameter is larger than the dimensions of the retaining collar 10033. If the retaining collar 10033 were a single piece, it would be permanently trapped between those other two larger elements. Nevertheless, the retaining collar 10033 is desirable as the forward stop for the blade holder 600. In an embodiment of the invention, this situation is addressed by making retaining collar 10033 in two parts, 10033A, 10033B. The two halves of retaining collar 10033 may abut each other and can have smooth or machined surfaces for such abutment. It can be seen that, in this embodiment, there is an external helical thread on retaining collar 10033 around the external surface of retaining collar 10033. It can be noted that the possible process of machining a single retaining collar 10033 and then cutting it in half would leave an undesirable gap equal to the kerf thickness of the cutting process, which would result in a part that would not be truly round and would not have threads that are perfectly continuous. Accordingly, in an embodiment of the invention, the retaining collar 10033 can be manufactured as two separate parts. It is possible either to abut two separate parts (with the parts having smooth or machined surfaces for such abutment) and then perform the machining including external threading. Alternatively, it is possible to manufacture the two halves separately if sufficient care is taken to make the external threads continuous. Disengageable alignment or mating features, such as pins and corresponding holes, may be provided in 10033A, 10033B to help align retaining collar parts 10033A, 10033B with each other.

It can be noted that the resilient material 10142 experiences the same situation, regarding installation, as retaining collar 10033, in that it occupies a smaller diameter while the blade holder 600 has a larger diameter forward and a larger diameter rearward of resilient material 10142. However, it is believed that resilient material 10142 may be sufficiently deformable so that it could be provided as a stretchable ring, or it could be provided as a ring with one split in it, or it could be provided in some other geometry that is easily installable.

Load Transfer Involving the Blade Holder

As is also discussed elsewhere herein, the blade holder 600 may be capable of transmitting to blade 40 load in a forward direction. In an embodiment of the invention, the osteotome 10 may be capable of generating load on the blade 40 in a forward direction as a result of impact of an impact piston, such as spherical piston 100, on a surface of blade holder 600.

After such contact or impact of spherical piston 100 with a surface of blade holder 600, spherical piston 100 may leave contact with blade holder 600 through any one or more of several mechanisms. First, spherical piston 100 may rebound or bounce back away from blade holder 600 due to local elasticity of the regions of spherical piston 100 and blade holder 600 that are involved in the impact. Additionally, spherical piston 100 may be driven in a rearward direction by the action of piston return spring 400 on spherical piston 100, possibly through the intermediary of piston washer 10085. Finally, there may be a return force generated on spherical piston 100 by the compression of gas forward of spherical piston 100 during the forward motion of spherical piston 100. The magnitude and timing of this last effect may be influenced by the plumbing and valving and timing in regard to the region of gas that is forward of spherical piston 100, which might either trap gas in that forward region or release gas from that forward region. Any or all of these three mechanisms may cause the spherical piston 100 to depart from blade holder 600, which stops the imposition of forward-directed load on the blade holder 600.

Rearward-directed load on the blade holder 600 may come from resilient material 10142 described elsewhere herein.

Blade Holder Slot for Receiving Blade

As described elsewhere herein, the gripping portion 42 of the blade 40 may have a generally "V" shaped cross-section with a rounded vertex of the "V" shape. In addition, the gripping portion 42 of the blade 40 may further comprise a shoulder 426 such that the proximal portion of the gripping portion 42 may be narrower than the more distal portion of the gripping portion 42. The transition between the wider portion and the narrower portion of gripping portion 42 may comprise a surface that is generally perpendicular to the axis of the blade 40.

The blade holder 600 may comprise, on its front end, an axially extending slot 642 suitable to receive the gripping portion 42 of the blade 40. The cross-sectional shape of the axially extending slot 642 in blade holder 600 may generally resemble the generally rounded-"V" shaped cross-sectional shape of the gripping portion 42 of the blade, with clearance appropriate so that the gripping portion 42 of the blade 40 may slide into the axially extending slot 642. Specifically, the face-to-face dimension of the slot 642 may be somewhat larger than the corresponding thickness of the blade 40, in order to provide clearance for the blade 40 to slide into the slot 642 of the blade holder 600. An entrance feature to the slot 642, in the form of a fillet or corner radius, may be provided in places desired.

If the gripping portion 42 of the blade 40 has a cross-sectional shape that is generally a rounded "V" shape, there may be an included angle between the two legs of the "V." In such situation, the slot may also be a rounded "V" shape in which the included angle between the two legs of the "V" of the slot may be substantially equal to the included angle between the two legs of the "V" of the gripping portion 42 of the blade 40.

In an embodiment of the invention, the rounded vertex of the "V" in the slot 642 in blade holder 600 may be more generally recessed or more spacious than the actual dimensions of the rounded vertex of the "V" of the gripping portion 42 of blade 40. This may provide ease of installing the blade 40 into the blade holder 600, or it may provide ability to accommodate inaccuracies in the radius of curvature of the rounded vertex of the blade 40. The axially extending slot 642 may have a first straight leg and a second straight leg and, at an inner surface of the "V," may have a recess that is more spacious than a corresponding rounded vertex surface of the blade, and at an outer surface of the "V," similarly may have a recess that is more spacious than a corresponding rounded vertex surface of the blade.

The distal surface of the blade holder 600 may have a surface that lies in a plane that is perpendicular to the longitudinal axis. The shoulder 426 surface of gripping region 42 of blade 40 that is generally perpendicular to the longitudinal axis of gripping portion 42 may touch the distal surface of the blade holder 600, which may be generally perpendicular to the longitudinal axis. This contact may serve to transmit force especially impact force in the forward direction from the blade holder 600 to the blade 40 through shoulder 426 of gripping portion 42 of blade 40.

If there is force being transmitted from the blade holder 600 to the blade 40 in the rearward or retrograde direction, transmission of that force from the blade holder 600 to the blade 40 may occur through the plunger 1422 to the slot 422 in the blade 40.

Thus, there are two ways in which load can be transferred, depending on the direction of the load. Load transfer can be accomplished by a combination of direct transfer to the blade 40 through essentially normal contacting surfaces in the forward direction, and for retrograde pullback, transfer through a wedge action against a side of a hole such as hole 422. Action on the plunger 1422 urging the gripping region 42 of blade 40 toward the corresponding surface of the slot 642 may accomplish two things. It may urge blade 40 rearward through the wedging action of the tip of plunger 1422 on hole 422, which may directly transmit rearward force to gripping region 42, which may keep the shoulder 426 of blade 40 snug against the forward surface of blade holder 600 so that load transmission in the forward direction occurs well. This same action may directly transmit retrograde force to gripping region 42 of blade 40. Also, plunger 1422 may urge gripping portion 42 of blade 40 into contact with one of the "V" shaped surfaces of the interior of slot 642. This urging and contact and associated friction may anchor the blade 40 in multiple directions, including anchoring blade 40 against possible small rotation in any direction of rotation. The "V" cross-sectional shape of the gripping portion 42 of blade 40 may provide the blade 40 some bending stiffness against the downward force applied by plunger 1422.

Plunger

Plunger 1422 may be a generally cylindrical component on at least some of its exterior and may have a tip that is conical or frustoconical or otherwise converging and having external surfaces that are angled with respect to the axis of plunger 1422. The plunger 1422 may have a tip that is tapered at an angle of about 45 degrees with respect to the longitudinal direction of the plunger 1422, which would correspond to an included tip angle of about 90 degrees. More generally, other angles are possible, such as the angle with respect to the longitudinal direction of the plunger being in the range of from 30 degrees to 60 degrees.

Plunger 1422 may be constrained so that it may move within a track or hole in blade holder 600, with the track or hole being oriented in a generally radial direction of motion with respect to the blade holder 600 or perpendicular to the longitudinal axis of blade 40. Plunger 1422 may interact with gripping region 42 of blade 40 to help position blade 40 as described elsewhere herein. Plunger 1422 may capture blade 40, may register a position of blade 40, and may exert force on blade 40 both in the axial direction and in a direction to urge the flat face of blade 40 against a corresponding flat face of blade holder 600.

Plunger 1422 may be movable between a locking configuration and a non-locking configuration. In the locking configuration, plunger 1422 may be in a more radially-inward location and may be suitable to engage with a blade 40 if a blade 40 is present in the blade holder 600, so as to lock the blade 40 in the blade holder 600 and transmit force to the blade 40. In the non-locking configuration, plunger 1422 may be in a more radially-outward location and may be such that it does not engage with the blade 40 and the blade 40 is free to move within the slot 642 in blade holder 600.

Plunger 1422 may be spring-biased by a spring such that the spring urges the plunger 1422 to tend to occupy the non-locking configuration. The spring may be such that in order for the plunger 1422 to occupy the locking configuration it is necessary to compress the spring.

Plunger 1422 may have an overall component and an insert 1423. The overall component may be made of a material that is hard but resilient, because it experiences a significant amount of vibration during use. If the overall component of the plunger 1422 is either too hard or too soft it will wear quickly. This component is currently made from Stainless Steel Grade Custom 455, which has an appropriate balance of properties.

The insert 1423 may be made of a polymer either for properties of wear or low friction, or for properties of elasticity along the longitudinal direction of the plunger and insert 1423. The elasticity may help to maintain load on the blade 40 after the twist cam is in its locking position. An example of a suitable polymeric material for the insert 1423 is polyetheretherketone (PEEK). PEEK is almost the ideal material for this application. It has very high toughness, resistance to autoclave, low coefficient of friction, and very good compressive strength, especially the glass filled versions which we use. Other materials are also possible for this application, including Polysulfone (Udel), Polyetherimide (Ultem), Poyethersulfone (Veradel), and LCP (Vectra). We had previously used a metal surface with various coatings and geometries but we still experienced wear of the top of the plunger 1422. It has been found that a PEEK cylindrical insert 1423 as the wear element is quite suitable.

Twist Cam

Referring now to FIGS. 8A-8E, in an embodiment of the invention, there may be provided a twist cam 10037 disposed in relation to the blade holder 600. The twist cam 10037 may be rotatable between two extreme positions. One of the positions may define an unlocked condition in which the blade 40 is able to be inserted into or removed from the blade holder 600. The other position may be a locked condition in which the blade 40 is retained within the blade holder 600. Locking angular position and release angular position may be separated by, for example 90 degrees of rotation as illustrated, although of course other amounts of angular rotation are also possible. The two extreme angular positions may be defined by an internal groove that extends around a corresponding portion of rotatable locking collar. The internal groove may interact with a pin that protrudes from blade holder 600.

Twist cam 10037 may be urged preferentially to one of its two positions by chuck torsion spring 10041. One end of chuck torsion spring 10041 may be connected to blade holder 600 and the other end of chuck torsion spring 10041 may be connected to twist cam 10037. Chuck torsion spring 10041 may undergo torsion generally around the longitudinal axis (axis that is the center of rotational symmetry) of blade holder 600.

Twist cam 10037 may have an axis of rotation which may be at the center of those exterior features of the rotatable locking collar that are generally cylindrical or circular. For example, the exterior of rotatable locking collar may be a generally cylindrical surface with the exception of hand-gripping features, and that generally cylindrical surface may have an axis which may be the axis of rotation of rotatable locking collar with respect to the body of osteotome.

Twist cam 10037 may have, on its interior, a camming internal surface 375 that has a sliding and load transferring interaction with the top of plunger 1422, such that the interaction is in the nature of a cam. This camming internal surface 375 may be disposed suitably to interact with plunger 1422 so as to drive plunger 1422 in a centrally-inward direction or allow plunger to move in an outward direction. Such camming internal surface 375 may be non-axisymmetric with respect to the overall axis of rotation of twist cam 10037, such that for different angles of rotation of twist cam 10037, plunger 1422 is determined to be in different positions along the principal direction of plunger 1422. The various positions of plunger 1422 can either release blade 40 or constrain blade 40, as described elsewhere herein. For example, camming internal surface 375 may be generally cylindrical while being eccentrically located with respect to the overall features of twist cam 10037, having its own axis that is offset from the longitudinal axis of blade holder 600.

Other than camming internal surface 375 and external gripping features, the major features of twist cam 10037 may be generally axisymmetric around a twist cam axis, which may coincide with the longitudinal axis of blade holder 600.

Dimensional Interrelationships

Figure 8A:
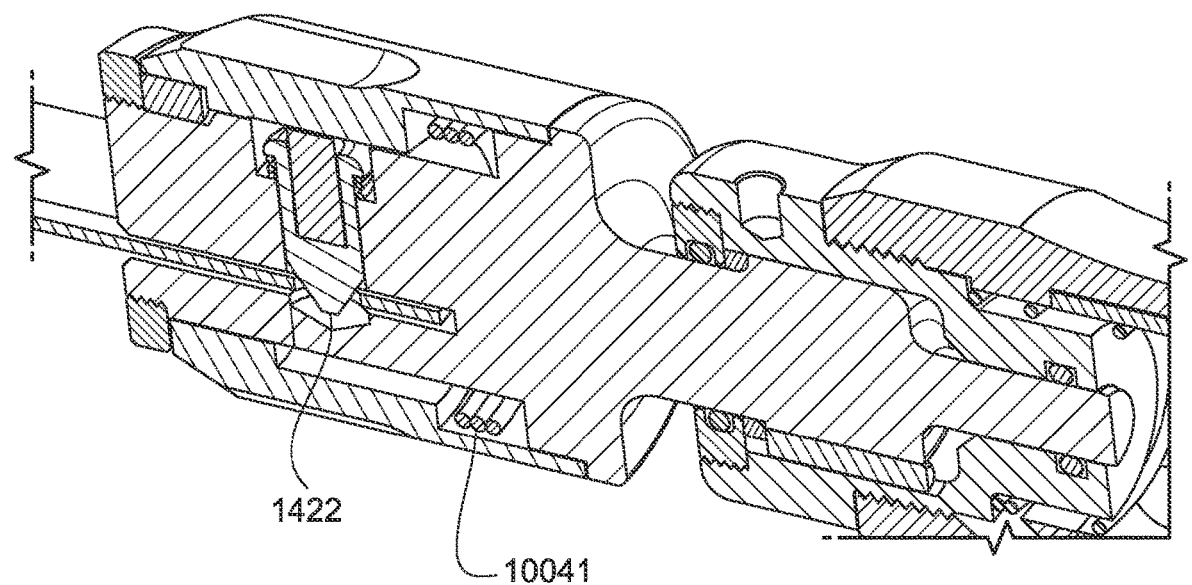
Figure 8B:
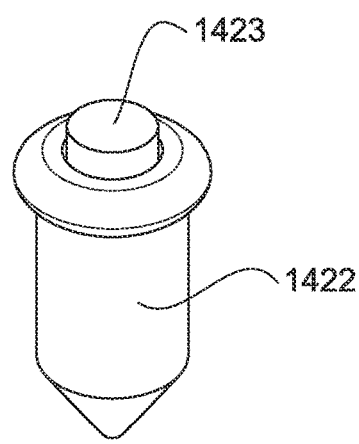
Figure 8C:
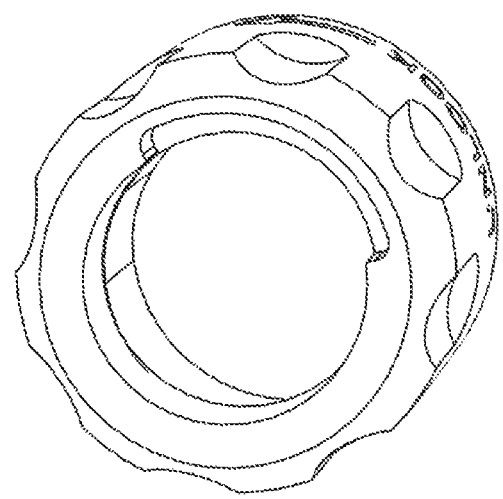
Figure 8D:
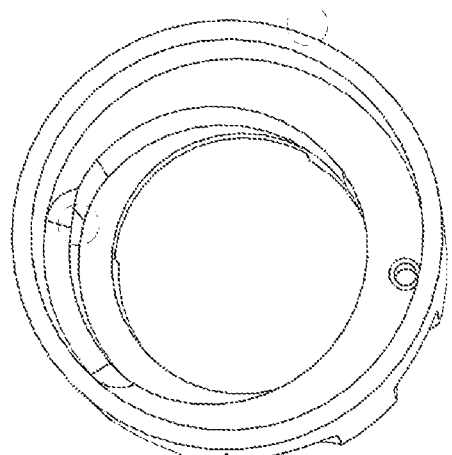
Figure 8E:
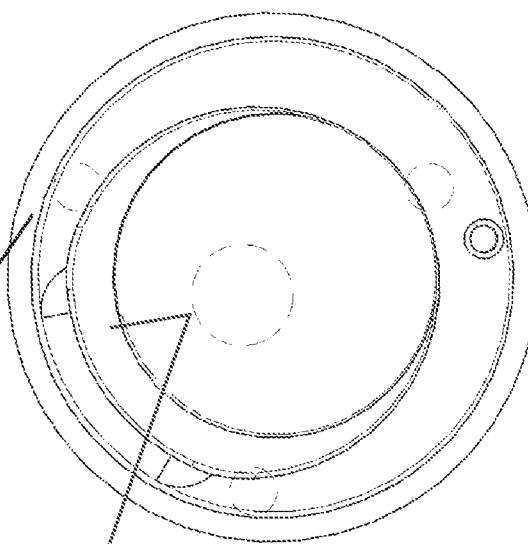

Dimensional interrelationships may be such that when the shoulder 426 of blade 40 abuts the front surface of the blade holder 600, the hole 422 in blade 40 is positioned such that plunger 1422 contacts the rear edge of hole 422 in blade 40 but does not contact the front edge of hole 422 in blade 40, or contacts the rear edge of hole 422 in blade 40 before it contacts the front edge of hole 422 in blade 40. This is illustrated in FIG. 8A, where the plunger 1422 is shown slightly interfering with the blade 40 at the rear of the hole 422 but not at the front of the hole 422.

Trigger and Flow Paths

Figure 9A:
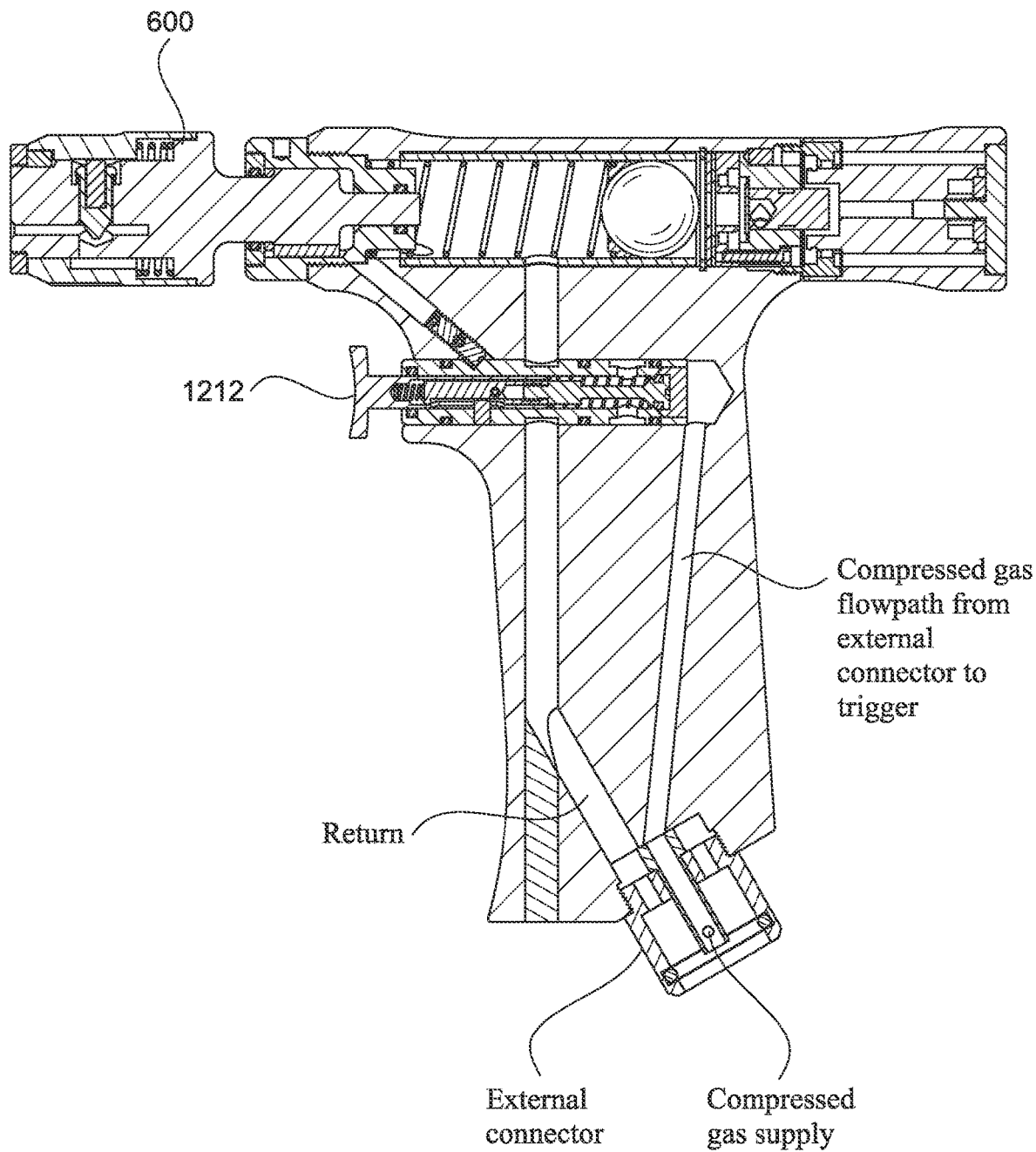
Figure 9B:
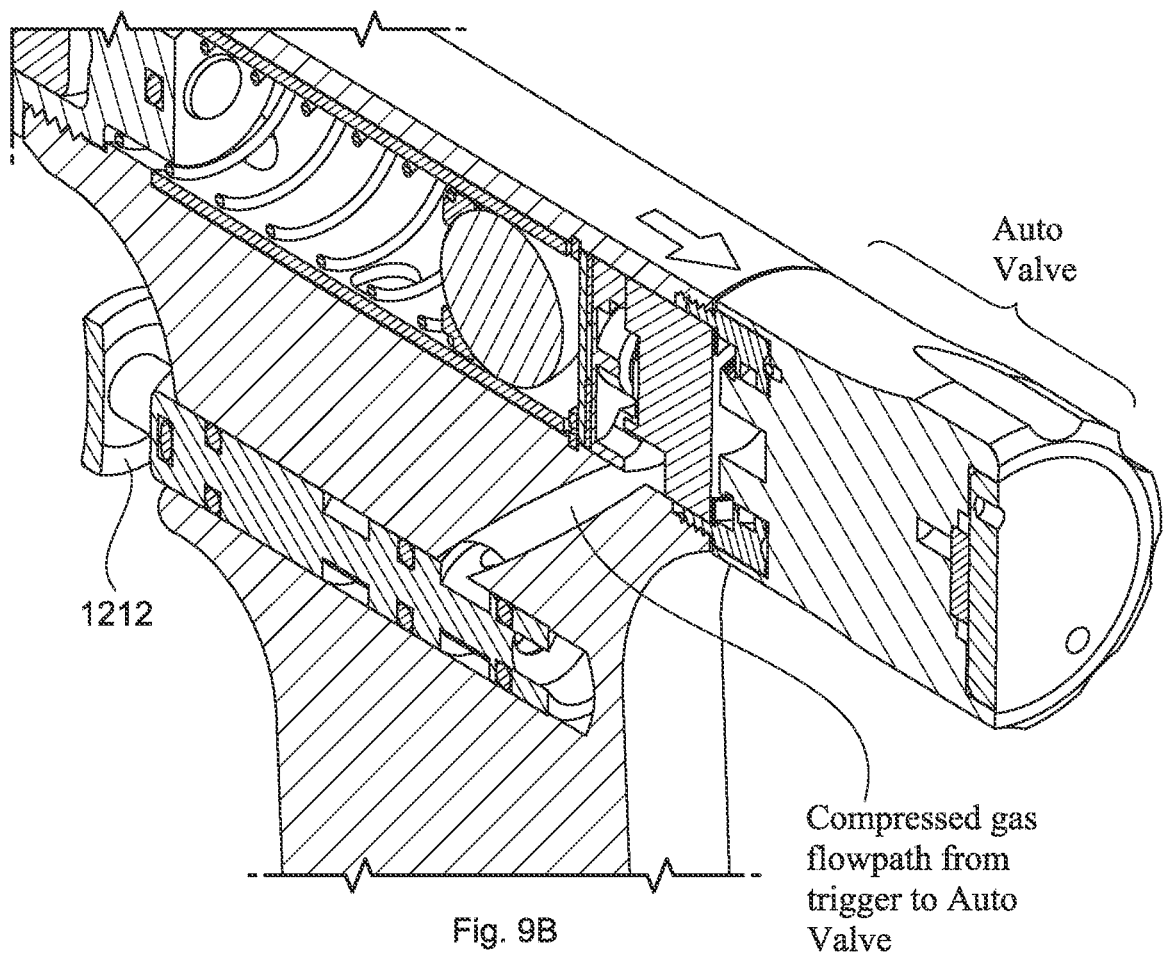

Referring now to FIGS. 9A-9B, there may further be provided a trigger 1212, which may be located in handle portion of osteotome 10 and may be suitable to be operated by the user. The trigger 1212 may act as a switch in the flowpath of the compressed gas that powers the osteotome 10. In the overall flowpath of gas through the osteotome 10, the trigger 1212 may be located upstream of the portions of the flowpath that generate mechanical impact, such as spherical piston 100. In an embodiment of the invention, the trigger 1212 functions generally as an on-off switch.

Operational Characteristics

During use, spherical piston 100 may be exposed on its rearward (right hand side in the illustrated orientation such as in FIGS. 1B-1E) to compressed air or other gas, urging spherical piston 100 to move forward (leftward as illustrated). Spherical piston 100 may move sufficiently forward to impact the blade holder 600. During continuous (repetitive) operation, the spherical piston 100 may oscillate back and forth within the cylinder at a rate of between 100 and 4000 strokes per minute. The spherical piston 100 may cover a stroke distance of between 0.5 inch and 4.0 inches, while delivering impact forces to a blade holder 600 at the end of each power stroke. In an embodiment of the invention, the spherical piston 100 impacts the blade holder 600 which in turn holds the blade 40 and transfers forces to the blade 40. The spring 400 between the spherical piston 100 and the distal end of the cylinder compresses during the power stroke and, during the return stroke, exerts force on the spherical piston 100 to push it back to its starting position. The relationship between the osteotome 10 and the blade holder 600 may allow a cutting excursion of between 0.001 inch and 1.000 inches. The cutting excursion may generally be smaller, often significantly smaller, than the distance of motion of the spherical piston 100 during a stroke. The spherical piston 100 may have a diameter of between 0.5 inch and 1.5 inch. The supply pressure of the gas is typically 100+/−30 psig. Following is a set of preferred parameters for a preferred embodiment:

- Rulon lined cylinder
- Tungsten carbide ball bearing Piston with a diameter of 0.750 inch and a surface finish of 8 micro inches rms
- Piston is spring loaded with a spherically shaped cupped washer that cradles
- Piston on one side and fits flush against piston return spring on the other side
- Piston impacts a blade holder which the blade mounts into. Blade holder allows a cutting excursion of 0.120 inches Geometry of Flow Paths for Gas Inside the Osteotome As Illustrated, the Body of the Osteotome 10 May be Generally Solid and of a suitable shape to be held by a user's hand. Although the body may be generally solid, there may be flowpaths within the body, such as may be created by drilling intersecting holes. First, there may be an external connection for supply and discharge of compressed gas such as compressed air. The external connection may be at the lower rear end of the osteotome 10. The connection may be both a supply connection to bring compressed gas to the osteotome 10, and a discharge or exhaust connection to carry discharged gas away from osteotome 10. Both supply and discharge may be accomplished by a common hose. The discharge may be through a hose to avoid discharging gas in the vicinity of the surgical site, such as for sterility reasons. The supply hose and the discharge hose, and the respective connections, may be concentric/coaxial with each other. As illustrated, the supply hose is the central hose and the discharge hose is disposed around the supply hose so that the discharge flowpath is an annular shape surrounding the supply hose. This is shown in FIG. 9A, which is a cross-section taken at the midplane of osteotome 10. Of course, other arrangements are also possible.

As illustrated, after the supply gas enters the osteotome 10 at the external connection, the supply gas proceeds to the trigger mechanism, which functions as a switch for the compressed gas. The flowpath from the external connector to the trigger mechanism is shown as being located generally in the midplane of the osteotome 10, although of course other locations would also be possible.

The compressed gas supply is shown as entering the trigger mechanism at the rear of the trigger mechanism. The trigger mechanism may be a form of spool valve, in which a sliding element determines whether any open area is available for flow of the compressed gas. As illustrated, within the trigger mechanism gas flows in a forward direction and then leaves the trigger mechanism so as to proceed to the Auto Valve.

The flowpath for compressed gas to flow from the trigger 1212 to the Auto Valve is shown as being located generally in an orientation that is not contained in the midplane of the osteotome 10 (i.e., not visible in FIG. 9A). The flowpath is shown as being a generally straight line but not purely in any single major direction of osteotome 10. This flowpath is shown in FIG. 9B in a cross-section of osteotome 10 where the sectioning plane is parallel to the midplane of osteotome 10 but is located slightly to the left of the actual midplane (left being defined with respect to a forward-looking user). The gas that has passed the trigger 1212 flows through the illustrated diagonal flowpath from the spool void near the trigger, to the Auto Valve.

In general, upon reaching the Auto Valve, the compressed gas may enter the Main Cylinder. The Auto Valve contains Auto Valve Disc 10027. Auto Valve Disc 10027 is capable, depending on its position, of either blocking or allowing the passage of compressed air from Auto Valve into the Main Cylinder. Several operating modes are possible depending on the position of the knob in the Auto Valve, as described elsewhere herein.

Figure 9C:
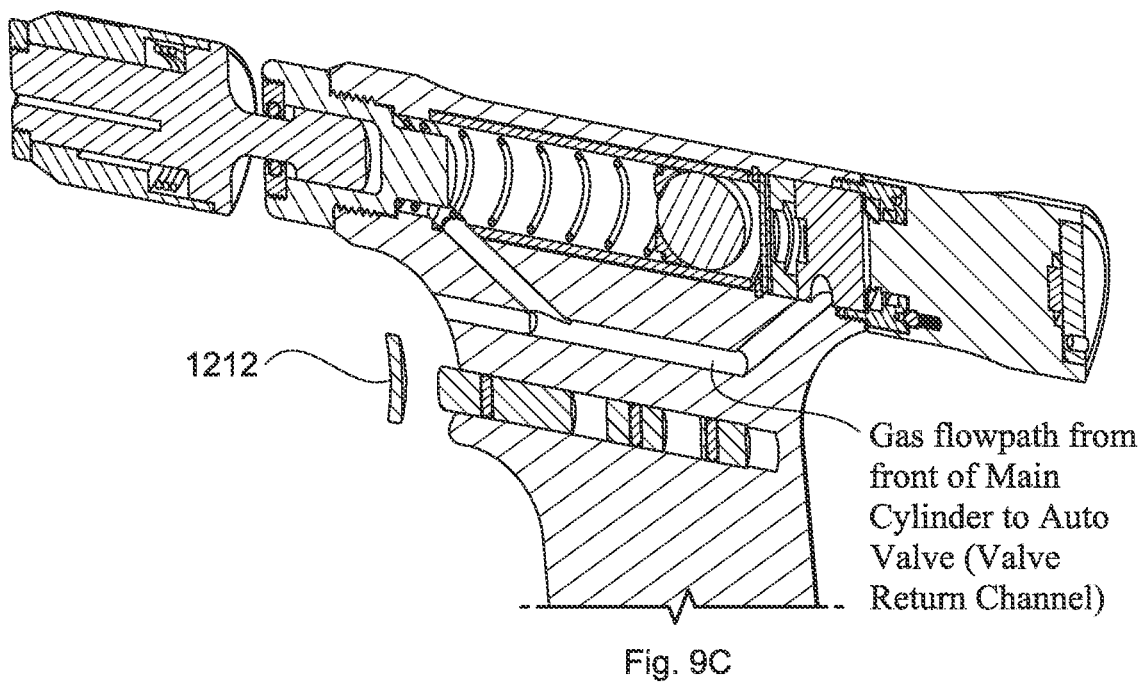
Figure 10F:
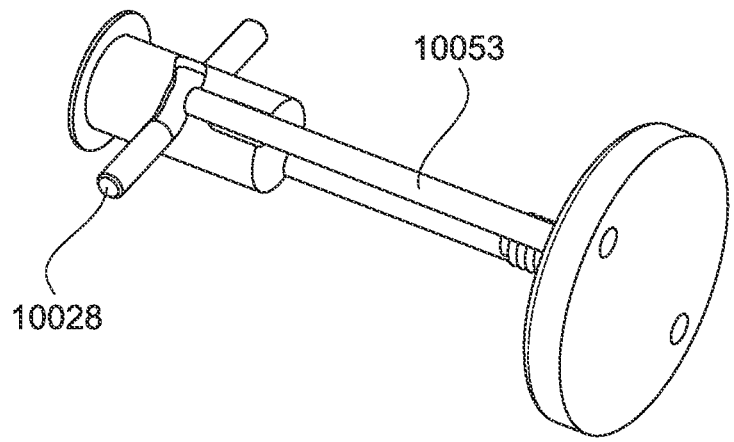
FIGS. 10F-10I show knob dowels associated with the Auto Valve Cam, for various positions of the Auto Valve Cam.
Figure 10G:
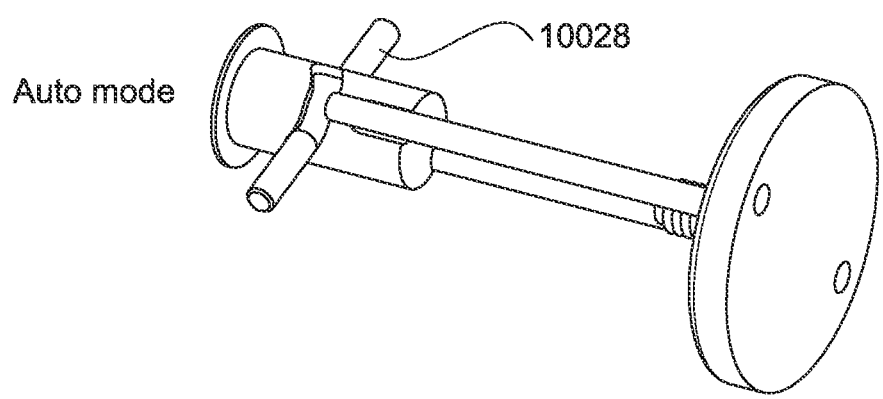
Figure 10H:
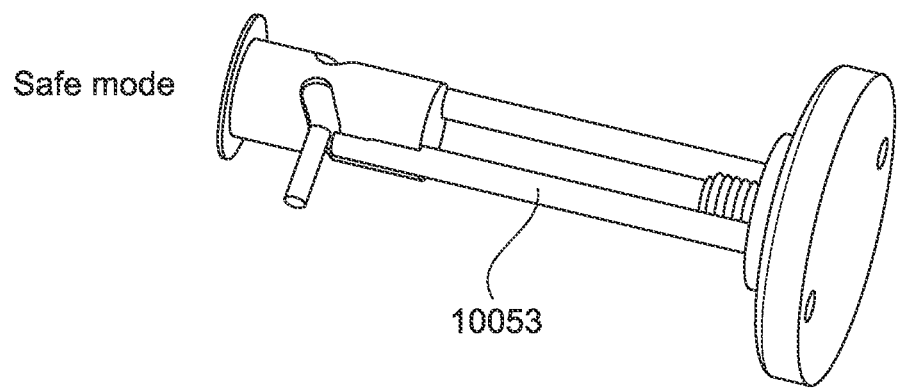
Figure 10I:
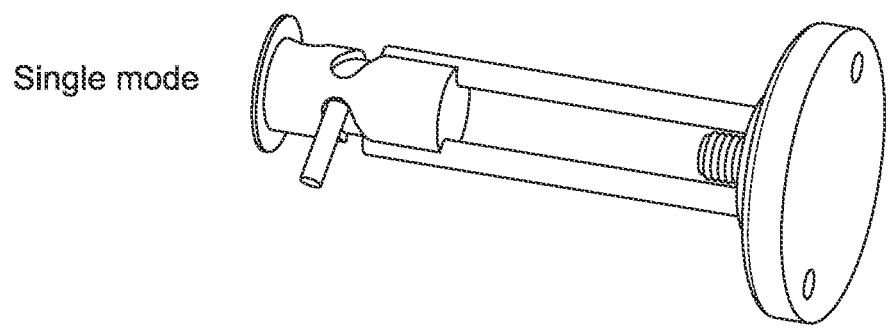

Another flowpath may also be provided within the body of osteotome 10. This flowpath may connect a forward region of the Main Cylinder with a region of the Auto Valve. As illustrated, it is shown that this flowpath is located generally in an orientation that is not contained in the midplane of the osteotome 10. In FIG. 9C, this flowpath is shown in a cross-section of osteotome 10 where the sectioning plane is parallel to the midplane of osteotome 10 but is located to the right of the actual midplane (right being defined with respect to a forward-looking user). This flowpath is shown as being made by three individual drilled holes that intersect so as to from a continuous path, although other designs are also possible.

Auto Valve Cam

Auto Valve Cam 10024 is illustrated in FIGS. 10A-10I. The Auto Valve Cam 10024 may have a groove in its circumferential surface that cooperates with a pin (Auto Valve Cam Dowel) 10028 riding in the groove. As the Auto Valve Cam 10024 changes its rotational angle, the pin 10028 cooperating with the groove causes the Auto Valve Cam 10024 to change its translational position along its axial direction (which is also its axis of rotation). This translational position of Auto Valve Cam 10024 either permits Auto Valve Disc 10027 to be rearward and allow flow of gas into Main Cylinder, under appropriate conditions; or it presses Auto Valve Disc 10027 against an entrance to the Main Cylinder so as to block flow of gas into the Main Cylinder (in Safe mode). Also, Auto Valve Cam 10024 has a blind axial hole entering from its front, and also has therethrough one angled hole that intersects the blind axial hole. These two holes in combination provide an optional flowpath that is used during Auto mode as described elsewhere herein.

As illustrated, for the two positions, Auto and Single, which are accessed at the extreme ends of the cam groove, the axial position of the groove in the Auto Valve Cam 10024 corresponding to those rotational positions of Auto Valve Cam 10024 are the same as each other, which means that the axial position of the Auto Valve Cam 10024, and the rest position of the Auto Valve Disc 10027 is the same for the Auto mode and for the Single mode. This equal-ness of positions is as illustrated, but of course it also is possible that those positions could differ from each other if desired. What does differ between Auto mode and Single mode is that the differing rotational positions of Auto Valve Cam 10024 causes a particular gas flow path to be open in one of those modes and closed in the other of those modes.

The Auto Valve Cam 10024 is able to be rotated among its various permitted positions within the stationary Auto Valve body to obtain the desired mode of operation. The Auto Valve Cam has two V shaped grooves radially along its outside perimeter which ride upon two fixed pins attached to the Auto Valve body. By rotating the Auto Valve Cam 10024, the Valve Return Channel can either be aligned with the hole in the Auto Valve Cam for Multi Stroke mode or not-aligned for Single Stroke mode.

The interaction of Auto Valve Cam 10024 with Auto Valve Cam Dowels 10028, shown in FIGS. 10F-10I, causes axial motion of the Auto Valve Cam 10024 along the length of the pins. The Auto Valve Cam 10024 can be expected to translate along its axial direction due to the action of following the side pins that engage the groove in the Auto Valve Cam 10024. The knob has an axial position that is fixed, so the changing distance (in the axial direction) between the Auto Valve Cam 10024 and the knob can be accommodated by sliding of the Auto Valve Cam 10024 along Knob Dowels 10053. Knob Dowels 10053 transmit the rotation of the knob to Auto Valve Cam 10024.

Exhaust Gas Flowpath

Figure 11A:
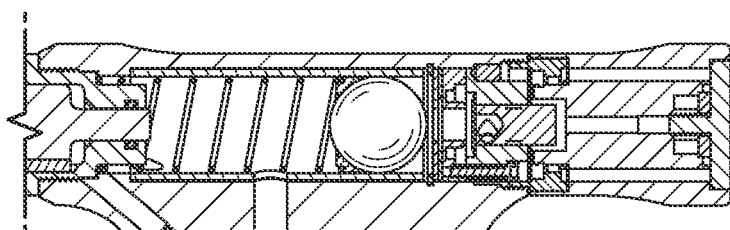
FIG. 11A-11C show exhaust air flow paths within the osteotome.
Figure 11C:
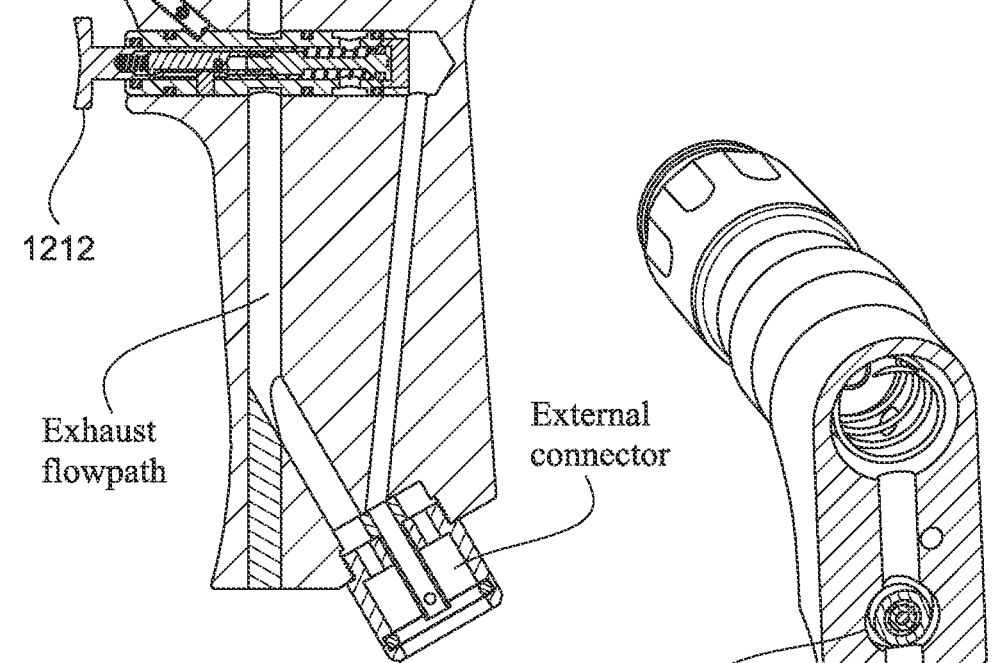
Figure 11B:
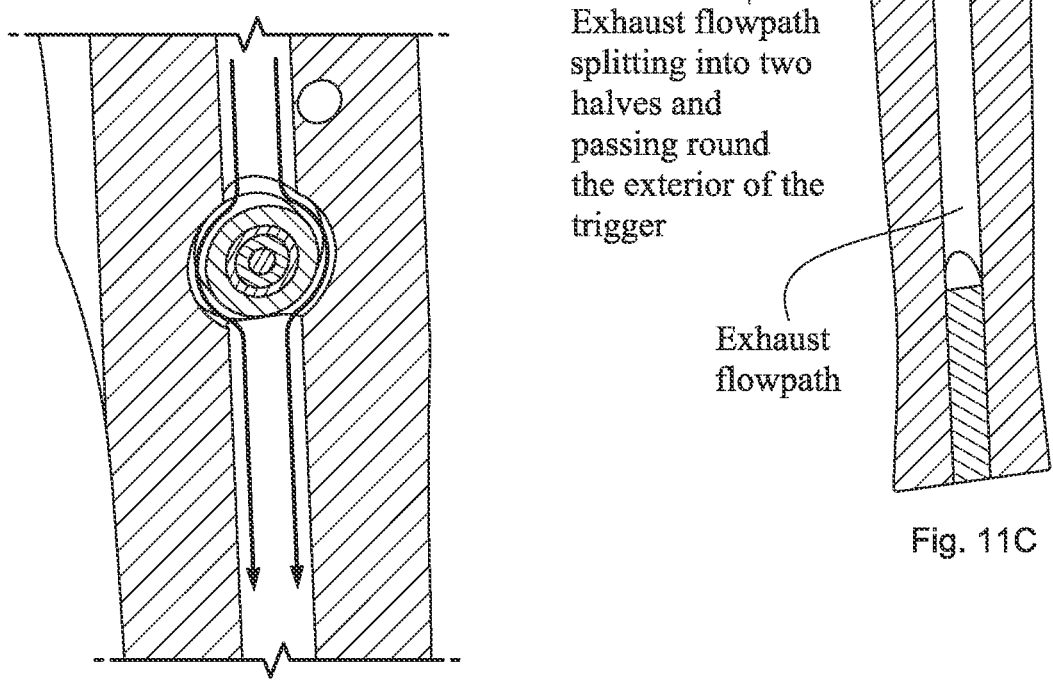
Figure 12A:
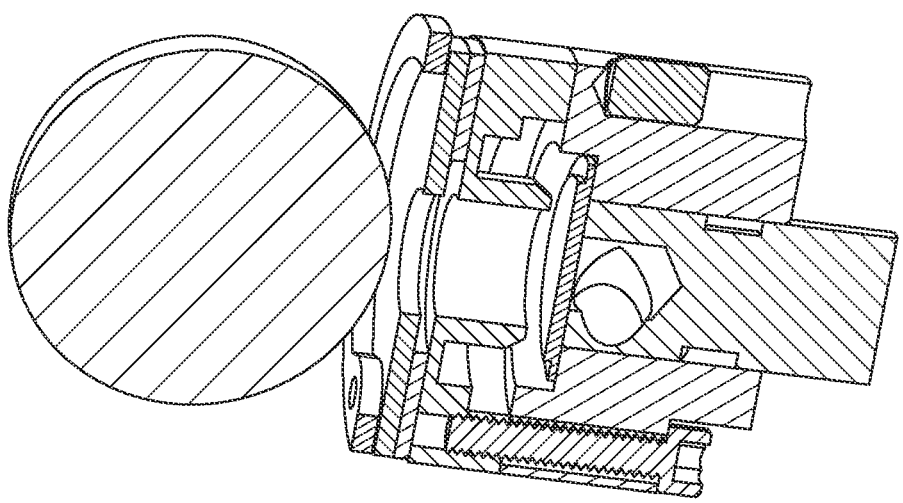
FIGS. 12A-12D show relationships between the spherical piston and the Auto Valve Cam.
Figure 12B:
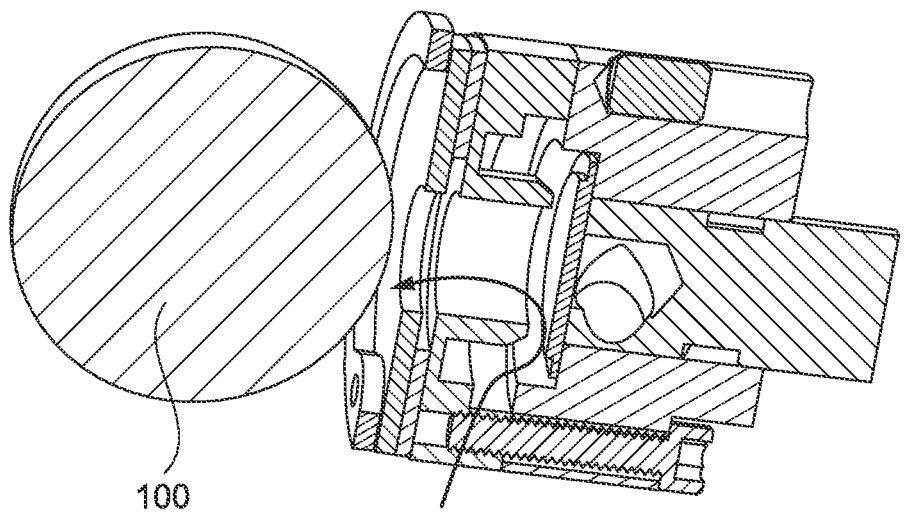
Figure 12C:
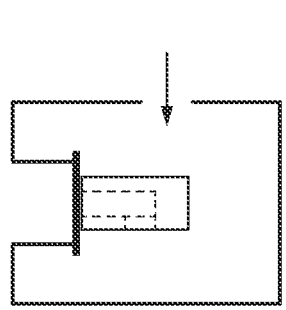
Figure 12D:
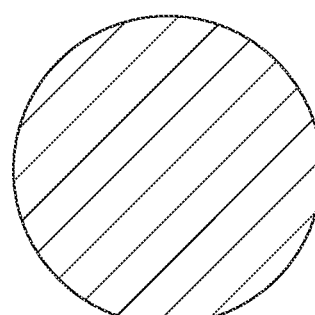

Also provided in osteotome 10 is an exhaust gas flowpath. The exhaust gas flowpath, as illustrated in FIGS. 11A-11C, intersects the Main Cylinder approximately perpendicularly approximately at the middle of the front-rear length dimension of the Main Cylinder. (It can be understood that variations in either or both of these design parameters are possible.) The exhaust gas flowpath may pass generally downward from the Main Cylinder to the external connector. As illustrated, the exhaust gas flowpath is on the midplane of the osteotome 10. As illustrated, the trigger 1212 also is on the midplane of osteotome 10. In order to allow exhaust gas flow to pass the trigger assembly, it is possible that a circumferential groove or recess can be provided in the trigger assembly, allowing exhaust gas to flow around the trigger assembly and continue towards the external connector. This is illustrated in FIGS. 11B and 11C.

FIGS. 12A-12D are illustrations of how the Auto Valve Cam 10024, in its retracted position, allows gas to flow into the Main Cylinder.

Modes of Operation

As illustrated in FIGS. 10A-10I, there are three designated rotational positions of the external knob and of the Auto Valve Cam 10024. These specific rotational positions may be determined by detents within the mechanism, and these specific rotational positions may be labeled on the exterior of the osteotome 10 visible to the user. Auto Valve Cam 10024 may be connected to or interact with a pair of knob dowels 10053 extending axially in a rearward direction from Auto Valve Cam 10024. Knob dowels 10053 may then connect to or interact with Mode Selection Knob 10048. Mode Selection Knob 10048, knob dowels 10053 and Auto Valve Cam 10024 may be connected to each other such that As illustrated, the designations for these three rotational positions are: Auto, Safe and Single. Safe may correspond to a configuration in which no compressed gas can flow through the osteotome and no actuation of the blade is possible, even if the trigger is pressed. In terms of position of labels and sequential positions of the knob and the operation of components within the mechanism, the Safe position may be located between the other two positions namely Auto and Single. Thus, in order for the knob and the state of the osteotome to pass from the Auto mode to the Single mode or from the Single mode to the Auto mode, it is necessary to pass through the Safe mode.

As illustrated, the amount of angular rotation of rear knob 10048 involved in going from Auto mode to Safe mode to Single mode is approximately 150 degrees, i.e., 75 degrees to shift from Auto mode to Safe mode, and another 75 degrees to shift from Safe mode to Single mode. However, it is of course possible that other angular choices could be made.

Safe Mode

In Safe Mode, the Auto Valve Cam 10024 is in the extended (forward) position such that it pushes and positions Auto Valve Disc 10027 so as to close off the port to the Main Cylinder, thereby preventing any gas from entering the Main Cylinder and rendering the Hand Piece inoperable. In the following illustration, the Auto Valve Disc 10027 is pressed against its seat so as to close off the flow of gas into the Main Piston, and this closure is static for as long as the osteotome 10 is in Safe mode.

Single-Stroke Mode

Referring now to FIGS. 13A-13D, the Handpiece 10 may have a nitrogen, or air, gas supply attached to it through the connector at the bottom of the Hand Piece (A). The Trigger 1212 may have a pressurized supply of gas flowing to it (B). When the Trigger 1212 is actuated the pressurized gas may flow through a channel (not seen in this illustration) to an Auto Valve (C).

Single-Stroke Mode, Position 1

FIG. 13A is an illustration of the Auto Valve in the Single Stroke Mode where the Auto Valve Cam is in the retracted position with its port not aligned with the Valve Return Channel (F). It allows the compressed gas at approximately 100 psig to flow freely through it to enter the Main Cylinder (D) and pressurize the volume behind the Piston. This causes the Piston 100 to travel forward, compressing the Piston Return Spring 400.

Single-Stroke Mode, Position 2

Referring now to FIG. 13B, as the Spherical Piston 100 reaches Position 2 and the pressure in front of the Spherical Piston 100 increases and some of the gas in the cylinder in front of the Spherical Piston 100 is exhausted through the exhaust channel (E). As the Spherical Piston 100 passes the exhaust channel, two things happen. The pressurized gas behind the Spherical Piston 100 begins to exhaust through the exhaust channel, reducing the force on the Spherical Piston 100, and the gas in front of the Spherical Piston 100 begins to compress the volume in front of the Spherical Piston 100 as well as in the Valve Return Channel (F). The Piston Return Spring 400 continues to compress.

Single-Stroke Mode, Position 3

Referring now to FIG. 13C, the momentum of the Spherical Piston 100 carries it through the Main Cylinder to impact the Blade Holder 600 at Position 3, at which point the Trigger is released by the user. This stops the flow of pressurized gas into the Main Cylinder.

Single-Stroke Mode, Position 4

Referring now to FIG. 13D, the Spherical Piston 100 is now forced by the compressed Piston Return Spring 400 and the pressure of the compressed gas in the volume in front of the Spherical Piston 100 to return to its starting point at Position 1, ready for the Trigger to be actuated again for another stroke.

In single stroke mode the air volume forward of the Spherical Piston 100 could (in certain embodiments) be directed towards the exhaust which would result in a greater pressure differential across the Spherical Piston 100 and more impact force on the tool holder 600. For pneumatic impactors in general, typically, a pneumatic impactor in single stroke mode has its exhaust somewhere around the middle of the length of the cylinder and so the exhaust will only exhaust the air up until the point the piston passed the exhaust pathway which is typically located near the middle of the length of the cylinder. From that point onward through the rest of the single stroke, the air in front of the piston is compressed by the piston, which creates a retarding force on the piston, which decreases the amount of impact actually delivered by the piston in the form of impact on the tool.

In contrast, in embodiments of the invention, during the later part of the single stroke, the gas that is trapped forward of the spherical piston 100 during the later part of the single stroke has a way of leaving that trapped region. This way of porting the air will decrease the pressure in that trapped region during the later part of the stroke, and therefore will allow greater impact forces to be generated during single stroke modes of operation. This can be influenced by flow configurations and timing within the Auto Valve.

Automatic or Multi-Stroke Mode

In automatic stroke (repetitive) mode, the content of the air volume forward of the Spherical Piston 100 is directed back toward the Auto Valve to make it automatic (repetitive).

Referring now to FIGS. 14A-14C, the Hand Piece may have a nitrogen, or air, gas supply attached to it through the connector at the bottom of the Hand Piece (A). The Trigger 1212 may have a pressurized supply of gas flowing to it (B). When the Trigger 1212 is actuated, the pressurized gas flows through a channel (not seen in this illustration because it is located in a different plane) to the Auto Valve (C). Shown in FIG. 14A is an illustration of the Auto Valve in the Auto or Multi-Stroke Mode where the Auto Valve Cam is in the retracted position with its port aligned with the Valve Return Channel (F).

Multi-Stroke Mode, Position 1

Initially the Auto Valve allows the pressurized supply gas to flow freely through it to enter the Main Cylinder (D) and pressurize the volume behind the Piston. This causes the Spherical Piston 100 to travel forward, compressing the Piston Return Spring 400. In the illustrated design, the Auto Valve is spring loaded. The Auto Valve Cam can also be turned so it extends axially and cuts off all gas flow to the Main Cylinder, which is the Safe mode.

Multi-Stroke Mode, Position 2

Referring now to FIG. 14B, as the Piston reaches Position 2 and the pressure in front of the Spherical Piston 100 increases, some of the gas in the cylinder in front of the Spherical Piston 100 is exhausted through the exhaust channel (E). As the Spherical Piston 100 passes the exhaust channel, several things happen. The pressurized gas behind the Spherical Piston 100 begins to exhaust through the exhaust channel, reducing the force on the Spherical Piston 100. The gas in front of the Spherical Piston 100 begins to compress the volume in front of the Spherical Piston 100 as well as in the Valve Return Channel (F). The Piston Return Spring 400 continues to compress.

Multi-Stroke Mode, Position 3

Referring now to FIG. 14C, the momentum of the Spherical Piston 100 carries it through to impact the Blade Holder 600 at Position 3. The gas in front of the Spherical Piston 100 has now increased significantly and has flowed through the Valve Return Channel. The Valve, being in Auto Mode, channels this high-pressure gas and directs it at the Auto Valve Disc within the Auto Valve to close off the compressed gas port into the Main Cylinder (G). This stops the flow of pressurized gas into the Main Cylinder, for a moment, reducing the pressure exerted on the Spherical Piston 100 in the forward direction as the gas in the cylinder between the Piston and the Auto Valve exhausts through the exhaust channel, allowing the Spherical Piston 100 to begin its return to Position 1.

As the Spherical Piston 100 begins to return, helped by the pressure in front of it and the compressed Piston Return Spring 400, it is reducing the pressure in the Valve Return Channel, reducing the pressure behind the Spherical Piston 100 and allowing the spring-loaded Valve Disc in the Auto Valve to return to its starting position.

As the Spherical Piston 100 returns to its starting position it increases the gas pressure on the Piston side of the Auto Valve, helping to open it up and allowing the high pressure gas to once again flow into the Main Cylinder, beginning the cycle again at Position 1.

The Hand Piece (osteotome 10) typically may operate from a nitrogen, or air, gas supply at 100 psi+/−30 psig attached to it through the connector at the bottom of the Hand Piece (A). In Auto mode, the frequency of striking can range from 100 to 4000 strokes per minute.

Additional Comments

In regard to materials, blade 10 may in general be made of a metal that is suitable for use in a surgical setting, such as an appropriate alloy of stainless steel. Splash guard 400 may be made of a polymer such as rubber or Acrylonitrile Butadiene Styrene (ABS). Structural parts may generally be made of a suitable metal, although other materials are also possible. Spherical piston 100 may be made of or may comprise tungsten carbide or another hard material. Cylinder liner 50 may be made of a low-friction polymer as described elsewhere herein.

Reference to cylinder include reference to the cylinder liner. Although the presence of a cylinder liner is desirable, it is possible for embodiments of the invention to have a cylinder without a liner, such as perhaps a coating rather than a liner.

The use of a low-friction material for the cylinder liner in the form of polytetrafluoroethylene (which is soft) makes it especially desirable to avoid gouging the cylinder liner such as might happen if the coil of the piston return spring 400 were to be pushed outward.

Tapering (of the plunger) near its tip is not limited to linear taper but rather could be taper of any profile. What has been referred to as the cylinder liner 50 could be the cylinder itself, which could be integral with the body of the osteotome.

In general, embodiments of the invention can achieve a usable lifetime, between maintenance, suitable for the device to be used in many tens of surgeries without maintenance or repair. It can be considered that a need for maintenance or repair is indicated by a noticeable decrease in the force generated by the device, with the decrease likely being caused by increased leakage of compressed gas from one side of the piston to the other side.

In general, any combination of disclosed features, components and methods described herein is possible.

All cited references are incorporated by reference herein.

Although embodiments have been disclosed, it is not desired to be limited thereby. Rather, the scope should be determined only by the appended claims.

We claim:

1. An osteotome, comprising:
a blade suitable to cut materials during surgery; and
a drive mechanism that either is configured to transmit a force to a force-transmitting component that transmits force to said blade, or is configured to transmit force directly to said blade,
wherein said drive mechanism comprises a cylinder having a cylinder liner, said cylinder liner being made of or comprising a cylinder liner material, and wherein said drive mechanism further comprises a spherical piston, said spherical piston being movable within said cylinder liner, said spherical piston being made of or comprising a piston material,
wherein a coefficient of sliding friction of said cylinder liner material with said piston material is less than 0.20, or a coefficient of sliding friction of said cylinder liner material with itself is less than 0.20, and
wherein said cylinder liner has an internal surface having a surface roughness of 125 microinches rms or smoother and said spherical piston has a surface roughness of between 5 and 20 microinches rms.

2. The osteotome of claim 1, wherein said cylinder liner is made as a separate part and comprises said cylinder liner material is different from a material of said cylinder.

3. The osteotome of claim 1, wherein said cylinder liner material comprises a fluoropolymer.

4. The osteotome of claim 1, wherein said cylinder liner material comprises a fluoropolymer containing particles of an additive selected from the group consisting of glass fibers, bronze particles, graphite particles, polyimide particles, and aluminum particles, or wherein said cylinder liner material comprises polytetrafluoroethylene filled with 15% glass fiber.

5. The osteotome of claim 1, wherein said cylinder liner has a wall thickness of at least 0.010 inch.

6. The osteotome of claim 1, wherein said cylinder liner has a sideways hole through said liner suitable to permit passage of a gas therethrough.

7. The osteotome of claim 1, wherein said surface roughness on said spherical piston is randomly oriented.

8. The osteotome of claim 1, wherein said spherical piston has a hardness of greater than approximately Rockwell C45.

9. The osteotome of claim 1, wherein a diametral clearance between said spherical piston and said cylinder liner is between 0.0001 inch and 0.010 inch.

10. The osteotome of claim 9, wherein said diametral clearance between said spherical piston and said cylinder liner is between 0.0004 inch and 0.0016 inch.

11. The osteotome of claim 1, wherein said spherical piston is configured to strike a surface of said force-transmitting component or of said blade during operation.

12. The osteotome of claim 1, wherein said osteotome is suitable to be driven by a compressed gas.

13. An osteotome, comprising:
a blade suitable to cut materials during surgery;
a drive mechanism that either is configured to transmit a force to a force-transmitting component that transmits force to said blade, or is configured to transmit force directly to said blade,
wherein said drive mechanism comprises a cylinder,
wherein said drive mechanism further comprises a spherical piston, said spherical piston being movable within said cylinder,
wherein said drive mechanism further comprises a piston return spring located within said cylinder,
wherein said drive mechanism further comprises a piston washer, said piston washer being located within said cylinder between said spherical piston and said piston return spring,
wherein said piston washer has a concave surface facing said spherical piston,
wherein said piston washer has a central opening therethrough;
wherein said piston washer comprises a head region and a neck region, said head region being larger in transverse dimension than said neck region, said head region facing said spherical piston, said neck region being suitable to occupy space inside a coil of said piston return spring; and
wherein said neck region has an outside diameter that is greater than an inside diameter of said coil of said piston return spring in an undeformed condition, but can fit inside said coil of said piston return spring when said coil is deformed radially outward, wherein said coil in said radially-outward-deformed condition still has a smaller outside diameter than an outside diameter of said head region.

14. The osteotome of claim 13, wherein said concave surface has an internal radius of curvature that is equal to or slightly greater than a radius of said spherical piston.

15. The osteotome of claim 13, wherein if said spherical piston is in contact with said piston washer, said spherical piston is able to transmit force to said force-transmitting component or is able to transmit force to said blade.

16. The osteotome of claim 13, wherein said piston return spring is a generally helical compression spring having an outside diameter and an inside diameter, said outside diameter of said piston return spring being smaller than an inside diameter of said cylinder.

17. The osteotome of claim 13, wherein said piston washer is axisymmetric and has an outside dimension that is less than a diameter of said spherical piston.

18. An osteotome, comprising:
a blade suitable to cut materials during surgery; and
a drive mechanism that is configured to transmit a force to a force-transmitting component that transmits force to a blade,
wherein said drive mechanism comprises a first cylinder and a first piston movable with respect to said first cylinder,
wherein said osteotome further comprises a second cylinder that is connected to and in a defined spatial relationship with said first cylinder, and said force-transmitting component comprises a second piston that is disposed to be able to receive impact force from said first piston, said second piston further extending to a narrower region and thence to a chuck, said chuck being suitable to grip said blade, said narrower region being narrower than said second piston,
wherein said narrower region is retained within said osteotome by a retaining collar that is threaded with an external helical thread,
wherein said retaining collar has a central hole therethrough having a central hole diameter that is smaller than a diameter of said second piston,
wherein said retaining collar comprises two parts each of which makes up approximately half of a circumference of said retaining collar and contains a portion of said external helical thread, wherein said two parts in combination form said external helical thread.

* * * * *